US012409328B1

(12) United States Patent
Rennaker

(10) Patent No.: US 12,409,328 B1
(45) Date of Patent: Sep. 9, 2025

(54) HYPOGLOSSAL NERVE STIMULATION

(71) Applicant: Board of Regents, The University of Texas System, Austin, TX (US)

(72) Inventor: Robert L. Rennaker, Sachse, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 565 days.

(21) Appl. No.: 17/715,159

(22) Filed: Apr. 7, 2022

Related U.S. Application Data

(60) Provisional application No. 63/171,744, filed on Apr. 7, 2021.

(51) Int. Cl.
*A61N 1/05* (2006.01)
*A61N 1/36* (2006.01)
*A61N 1/372* (2006.01)
*A61N 1/378* (2006.01)

(52) U.S. Cl.
CPC ....... *A61N 1/37235* (2013.01); *A61N 1/0556* (2013.01); *A61N 1/3611* (2013.01); *A61N 1/36139* (2013.01); *A61N 1/36157* (2013.01); *A61N 1/36171* (2013.01); *A61N 1/36175* (2013.01); *A61N 1/3787* (2013.01)

(58) Field of Classification Search
CPC ........................ A61N 1/37235; A61N 1/0556; A61N 1/3611; A61N 1/36139; A61N 1/36157; A61N 1/36171; A61N 1/36175; A61N 1/3787
See application file for complete search history.

(56) References Cited

U.S. PATENT DOCUMENTS

| | | | |
|---|---|---|---|
| 4,830,008 | A | 5/1989 | Meer |
| 5,146,918 | A | 9/1992 | Kallok et al. |
| 5,211,173 | A | 5/1993 | Kallok et al. |
| 5,215,082 | A | 6/1993 | Kallok et al. |
| 5,522,862 | A | 6/1996 | Testerman et al. |
| 5,540,733 | A | 7/1996 | Testerman et al. |

(Continued)

FOREIGN PATENT DOCUMENTS

| | | |
|---|---|---|
| EP | 0404427 A1 | 12/1990 |
| EP | 0743076 A1 | 11/1996 |
| EP | 1524007 A1 | 4/2005 |

*Primary Examiner* — Eugene T Wu
(74) *Attorney, Agent, or Firm* — pH IP Law

(57) ABSTRACT

Systems and methods for hypoglossal nerve stimulation. Certain embodiments include a pulse generator, circuitry configured to receive an energy signal, a communication module, and a programming module. In certain embodiments, the first pulse generator comprises a first electrode and a second electrode, a pulse generator coil, and circuitry configured to receive an energy signal. In particular embodiments, the first pulse generator can be configured to be implanted directly on a hypoglossal nerve on a first side of the patient and configured to deliver stimulation energy to activate at least one branch of the hypoglossal nerve on the first side of the patient. The communication module can include a communication coil configured to communicate with the pulse generator coil in specific embodiments. The programming module can be configured to communicate programming instructions to the communication module, the programming instructions defining an attribute of the stimulation energy.

34 Claims, 25 Drawing Sheets

(56) References Cited

U.S. PATENT DOCUMENTS

| | | | |
|---|---|---|---|
| 8,401,651 B2 | 3/2013 | Caparso et al. | |
| 8,831,730 B2 | 9/2014 | Mashiach et al. | |
| 8,892,205 B2 | 11/2014 | Miller, III et al. | |
| 9,248,302 B2 | 2/2016 | Testerman et al. | |
| 9,849,289 B2 | 12/2017 | Mashiach et al. | |
| 10,029,098 B2 | 7/2018 | Papay | |
| 10,631,779 B2 | 4/2020 | Meadows et al. | |
| 2003/0040785 A1* | 2/2003 | Maschino | A61N 1/0556 607/118 |
| 2005/0085874 A1* | 4/2005 | Davis | A61N 1/37205 607/66 |
| 2005/0267547 A1* | 12/2005 | Knudson | A61N 1/36017 607/48 |
| 2007/0233204 A1* | 10/2007 | Lima | A61N 1/321 607/46 |
| 2013/0060110 A1 | 3/2013 | Lynn et al. | |
| 2015/0039046 A1* | 2/2015 | Gross | A61N 1/3756 607/42 |
| 2020/0147376 A1* | 5/2020 | Dieken | A61N 1/36139 |
| 2020/0254249 A1* | 8/2020 | Rondoni | A61P 11/16 |
| 2023/0172479 A1* | 6/2023 | Verzal | A61N 1/36078 607/42 |

\* cited by examiner

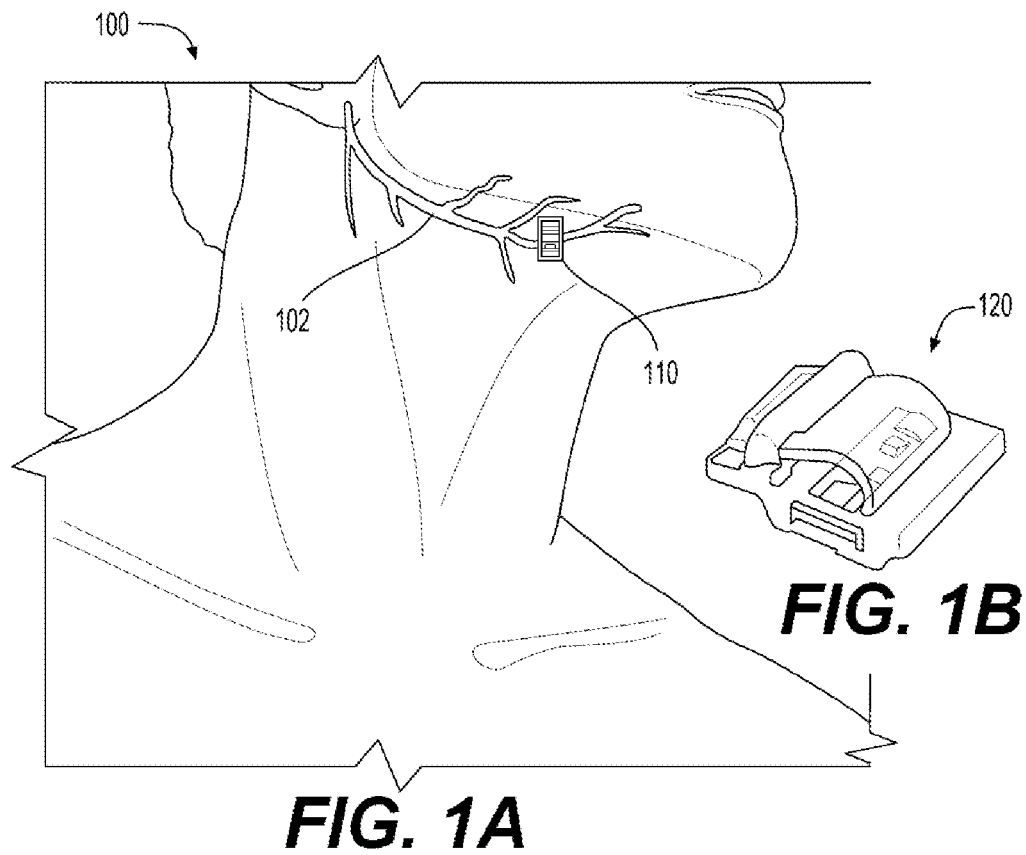
FIG. 1A
FIG. 1B
FIG. 1C

| SYSTEM COMPONENT | ReVive SYSTEM |
|---|---|
| IPG FIRMWARE | 5.0mA MAXIMUM |
| IPG FIRMWARE | OSA INDICATION |
| IPG CUFF | 1mm – 2mm DIAMETER |
| PCM FIRMWARE | UP TO COMMUNICATION WITH 4 DEVICES |
| PCM FIRMWARE | MAXIMUM 50% DUTY CYCLE |
| PCM | 7 cm x 5 cm OVAL FLEXIBLE COIL |
| PCM | >2000 mAh BATTERY (10 HOURS) |
| PCM | ADD SpO2, MICROPHONE & ACCELEROMETER |
| NECKBAND | POSITIONS COIL OVER HYPOGLOSSAL NERVE |
| NECKBAND | SMART PILLOW DURING SLEEP |
| APPLICATION | UPDATED FOR OSA |
| SYSTEM | AT-HOME DURING SLEEP |

*FIG. 1F*

| ReVive |
| --- |
| BY Xnerve |

✓ PCM CONNECTED        ✗ LOG OUT

| PCM ID# 0030420 | BATTERY 89% | OXYGEN SATURATION 98% | HEART RATE 72 BPM |

PATIENT SETTINGS

SLEEP DELAY (MIN)    30      ⬤⬤

ACCLIMATE      ⬤⬤

| COMFORT SETTINGS<br>+<br>4<br>−<br>TEST<br>2.9 | RIGHT SIDE<br><br>ID#: 098230351 | LEFT SIDE<br><br>ID#: 098230351 | COMFORT SETTINGS<br>+<br>4<br>−<br>TEST<br>2.9 |

CLINICIAN SETTINGS

| RIGHT SIDE ⬤⬤ | | LEFT SIDE ⬤⬤ | |
| --- | --- | --- | --- |
| STIMULATION PARAMATERS | | STIMULATION PARAMATERS | |
| CURRENT (mA) | 1 | CURRENT (mA) | 1.5 |
| PULSE WIDTH (us) | 100 | PULSE WIDTH (us) | 200 |
| FREQUENCY (Hz) | 30 | FREQUENCY (Hz) | 350 |
| THERAPY PARAMETERS | | | |
| RESPIRATION RATE (BPM): | 16 | RR LOWER LIMIT (BPM): | 12 |
| RR UPPER LIMIT (BPM): | 22 | STIMULATION %: | 50 |
| ACCLIMATE | | ACCLIMATE | |
| START CURRENT (mA) | 1.5 | START CURRENT (mA) | 2.0 |
| STEP SIZE (mA) | 0.5 | STEP SIZE (mA) | 0.6 |
| STEP TIME (min) | 5.0 | STEP TIME (min) | 8.0 |

MANUFACTURER SETTINGS

FIRMWARE UPDATES

[ R-IPG FWU ]    [ L-IPG FWU ]    [ HUB FWU ]

| ReVive V0.0.1    HUB V1    D-IPG V1.0    S-IPG V1.0 |

*FIG. 6*

HYPOGLOSSAL NERVE STIMULATION

CROSS-REFERENCE TO RELATED APPLICATIONS

This application claims priority to U.S. Provisional Patent Application 63/171,744, filed Apr. 7, 2021, the entire contents of which are incorporated by reference herein.

BACKGROUND

Sleep disordered breathing encompasses a number of illnesses including snoring, upper airway resistance syndrome (UARS) and obstructive sleep apnea-hypopnea syndrome (OSAHS). Obstructive sleep apnea (OSA) results when the tongue and soft tissue relax during sleep and move backwards in the throat resulting in partial or complete occlusion of the upper airway during sleep. This tissue causes an obstruction in the airway that partially (hypopnea) or completely (apnea) blocks the airway.

If the airway occlusion persists long enough, it results in a reduction in oxygen saturation, changes in heart rate, and eventually arousing the patient from sleep. In patients with moderate to severe OSA, the airway is compromised 15 or more times per hour. Untreated, moderate to severe OSA can result in excessive daytime fatigue, poor sleep, vehicular accidents, impaired short-term memory, hypertension, right-sided congestive heart failure, stroke, and the like.

The lack of oxygen arouses patients from sleep. Apnea-Hypopnea Index (AHI) measures the number of times per hour that results in partially or completely patient flow cessation and awakens the patient. An Apnea-Hypopnea Index of 15-30 is considered moderate OSA, and greater than 30 times per hour is considered severe OSA. Obstructive sleep apnea is the world's most common sleep disorder occurring in rates of up to 50% in some countries and affecting around 936 million people globally, of which 425 million people worldwide, who suffer from moderate to severe OSA, require treatment (Benjafield et al., Lancet Respir Med).

Options range from lifestyle changes such as weight loss and medical interventions, including Continuous Positive Airway Pressure (CPAP), Mandibular Advancement Devices, and traditional surgical interventions to remove soft tissue and remodel the back of the throat. CPAP is the first line treatment for 80% of patients diagnosed with moderate-to-severe OSA patients. CPAP has demonstrated efficacy in reducing the Apnea-Hypopnea Index. However, lack of compliance has been estimated to be between 29% and 83% (Kribbs et al., Am. Rev. Respir. Dis. 1993; Sawyer et al. Sleep Med. Rev. 2011; Weaver et al. Proc. Am. Thorac. Soc. 2008).

Mandibular Advancement Devices (MAD) are worn in the mouth and open the airway by forcing the mandible forward. MADs can cause discomfort, including teeth and jaw pain and tooth displacement, requires multiple and recurrent follow-ups with dentists to adjust or change the MAD, is less suitable for the severe OSA, and has low therapy efficacy (21% to 50%) (Hoffstein et al. Sleep Breath 2007).

In patients having difficulty with other treatments, surgical procedures for the nose (e.g., remove nasal tissue), throat (e.g., palate, tonsils, uvula) or mandible, can be a beneficial alternative. These are invasive procedures that irreversibly alter the patient's anatomy. Some procedures can last several hours, are painful, and require long recuperation periods. Given the low rate of efficacy, patients may need multiple procedures to reach therapeutic efficacy (Sher et al. Sleep 1996). Surgical procedures are often considered as a last resort option given the high complication rate.

Stimulation of any nerve can be uncomfortable. To reach therapeutic effect, hypoglossal nerve stimulation adjustments can take up to 6 months. In this disclosure, a system and method are provided for adjusting hypoglossal stimulation to allow a more rapid acclimation.

SUMMARY OF ILLUSTRATIVE EMBODIMENTS

The forgoing general description of the illustrative implementations and the following detailed description thereof are merely exemplary aspects of the teachings of this disclosure and are not restrictive.

In an embodiment, the present disclosure generally relates to methods for powering and communicating with one or more hypoglossal nerve Smart Wireless Implantable Pulse Generator (SWIPG), collectively the ReVive system. In some embodiments, the present disclosure relates to programming the ReVive system to permit the patient to adjust a combination of stimulation parameters on one or more IPGs to adjust the comfort associated with stimulation.

In some embodiments, the present disclosure includes methods for selectively activating one or more nerves related to tongue position to open the airway to treat obstructive sleep apnea.

In an embodiment, the ReVive system is configured to be used for stimulation of the hypoglossal nerve for treating Obstructive Sleep Apnea.

In an embodiment, the ReVive system is configured to be used to treat patients suffering from moderate to severe OSA (Apnea-Hypopnea Index greater or equal to 15 and less than or equal to 65).

In an embodiment, the ReVive system is configured to be in adult patients who have failed, not tolerated, or refused PAP treatments.

In an example, PAP failure is defined as inability to eliminate OSA, Apnea-Hypopnea Index remaining higher than 15 despite PAP usage.

In an example, PAP intolerance is defined as inability to use PAP at least 5 nights per week and 4 hours or more of use per night (guidelines definition).

Certain embodiments include a system for providing hypoglossal stimulation, the system comprising a first pulse generator, wherein the first pulse generator comprises at least a first electrode and a second electrode, a pulse generator coil and circuitry configured to receive an energy signal, the first pulse generator configured to be implanted directly on a hypoglossal nerve on a first side of the patient and configured to deliver stimulation energy to activate at least one branch of the hypoglossal nerve on the first side of the patient. In particular embodiments, the system comprises a communication module including a communication coil configured to communicate with the pulse generator coil, and a programming module configured to communicate programming instructions to the communication module, the programming instructions defining an attribute of the stimulation energy. In specific embodiments, at least one of the communication module and the programming module is configured to receive sensor data from a first sensor configured to sense at least one of heart rate, oxygen saturation, sleep sounds, patient movement, eye movement, and electrical activity of at least one of the brain and eye, and the attribute of the stimulation energy includes at least one of a current amplitude, current duration, a ramping profile, and a pause.

In certain embodiments, the pulse generator does not comprise a battery. In particular embodiments, the attribute of the stimulation energy includes at least one of a pulse width, pulse frequency, specified waveform shapes, rise time and fall time. In specific embodiments, the programming module is configured to adjust the attribute of the stimulation energy during a single night. In certain embodiments, the programming module is configured to adjust the attribute of the stimulation energy during multiple nights. In particular embodiments, the sensor data comprises a sleep position of the patient and wherein the system is configured to alert the patient when the sleep position is not the correct sleep position. In specific embodiments, the system is configured to calculate an oxygen desaturation index (ODI) or a Apnea-Hypopnea Index (AHI), and wherein the attribute of the stimulation energy is adjusted based on the ODI or the AHI.

Certain embodiments further comprise a carrier configured to couple to the pulse generator and to secure the pulse generator to the hypoglossal nerve wherein the carrier comprises: a housing, a strap comprising a plurality of adjustment members, and a retention member configured to engage the plurality of adjustment members. In particular embodiments, the housing comprises a first aperture proximal to the first electrode and a second aperture proximal to the second electrode. In specific embodiments, the housing comprises at least one spacer proximal to the first aperture and the second aperture. In certain embodiments, the first electrode and the second electrode each comprise a plurality of edges, and the at least one spacer is configured to position a hypoglossal nerve such that the hypoglossal nerve does not contact the plurality of edges of the first electrode and the second electrode when the carrier is secured to the hypoglossal nerve.

In specific embodiments, the at least one spacer comprises a central spacer between the first electrode and the second electrode. In certain embodiments, the strap comprises a tapered end configured for insertion into the retention member. In particular embodiments, the strap has a length sufficient to allow the strap to extend over one or more nerves and through the retention member such that the adjustment members engage the retention member when the tapered end extends ex vivo. In specific embodiments, the plurality of adjustment members are capable of deformation when the strap is secured around the hypoglossal nerve. In certain embodiments, the strap comprises a reduced thickness portion. In specific embodiments, the reduced thickness portion is less than 1.0 millimeters thick. In certain embodiments, the strap is formed from a material having a Shore A hardness of 40 or less. In particular embodiments, the pulse generator comprises a microprocessor.

In specific embodiments, the system further comprises a second pulse generator, having no battery, including at least a first and second electrode, a second pulse generator coil, and circuitry configured to receive an energy signal, the second pulse generator configured to be implanted directly on a hypoglossal nerve on a second side of the patient and configured to deliver stimulation energy to activate at least one branch of the hypoglossal nerve on the second side of the patient. In certain embodiments, the system further comprises a second sensor configured to detect a position of the patient, wherein the programming module is configured to modify the stimulation energy on at least one of the first pulse generator and the second pulse generator based on the position of the patient.

In particular embodiments, the system further comprises a second pulse generator, having no battery, including at least a first and second electrode, a second pulse generator coil, and circuitry configured to receive an energy signal, wherein the second pulse generator is configured to be implanted directly on the hypoglossal nerve on a second branch of the hypoglossal nerve on the first side of the patient and configured to deliver stimulation energy to activate at least another branch of the hypoglossal nerve on the first side of the patient. In specific embodiments, the pulse generator comprises an aperture configured to receive a strap to secure the pulse generator to the hypoglossal nerve. Certain embodiments further comprise a carrier configured to couple to the pulse generator and to secure the pulse generator to the hypoglossal nerve.

In particular embodiments, the carrier includes a body portion configured to secure the pulse generator to at least a first branch of the hypoglossal nerve and an arm portion extending from the body portion configured to isolate at least a second branch of the hypoglossal nerve from the first branch of the hypoglossal nerve. Specific embodiments further comprise a soft silicone rubber case with at least one suturing hole configured to be sutured to tissue and to hold the IPG in intimate contact with the hypoglossal nerve. In certain embodiments, the energy signal is at least one of electromagnetic energy and ultrasound energy. In specific embodiments, the pulse generator coil is a mechanical structure configured to transform ultrasound energy to generate the stimulation energy to activate the at least one branch of the hypoglossal nerve. Certain embodiments further comprise a wearable hub configured to position the communication module in relation to the pulse generator such that the pulse generator coil substantially aligns with the communication coil. In particular embodiments, the hub comprises a hub coil configured align with the pulse generator coil and a second hub coil the communication module to position the communication module in relation to the pulse generator such that the pulse generator coil substantially aligns with the communication coil.

In specific embodiments, the hub comprises a hub coil configured align with the pulse generator coil and at least one of a second hub coil configured to align with the communication module and a wired connection. In certain embodiments, the hub is configured to hold the first sensor to the skin of the patient, such that the first sensor can obtain a physiological reading.

Particular embodiments include a system for providing hypoglossal stimulation, the system comprising: a first pulse generator, having no battery, including at least a first and second electrode, a first pulse generator coil, and circuitry configured to receive an energy signal, the first pulse generator configured to be implanted directly on a hypoglossal nerve on a left side configured to deliver stimulation energy to activate at least one branch of the hypoglossal nerve on a first side of the patient; a second pulse generator, having no battery, including at least a first and second electrode, a second pulse generator coil, and circuitry configured to receive an energy signal, the second pulse generator configured to be implanted directly on a hypoglossal nerve on a right side configured to deliver stimulation energy to activate at least one branch of the hypoglossal nerve on the right side; a communication module including a communication coil configured to communicate with the pulse generator coil, the communication coil configured to communicate energy to the pulse generator and communicate programming instructions from an application; and a programming module configured to communicate programming instructions to the communication module; wherein at least one of the communication module and the programming module is configured to receive sensor data from a first sensor configured to sense at least one of heart rate, oxygen saturation, sleep sounds, patient movement, eye movement, and electrical activity of at least one of the brain and eye.

Specific embodiments include a method for providing hypoglossal stimulation acclimation, the method comprising: providing a hypoglossal stimulation system including: a first pulse generator, having no battery, including at least a first electrode and a second electrode, a pulse generator coil, and circuitry configured to receive an energy signal, the first pulse generator configured to be implanted directly on a hypoglossal nerve on a first side of the patient and configured to deliver stimulation energy to activate at least one branch of the hypoglossal nerve on the first side of the patient, a communication module including a communication coil configured to communicate with the pulse generator coil, the communication coil configured to communicate energy to the pulse generator, and a programming module configured to communicate programming instructions to the communication module; placing the first pulse generator directly on a hypoglossal nerve on a first side of the patient; sensing a physiological attribute of the patient using the first sensor; generating, by the programming module, a set of programming instructions defining an attribute of the stimulation energy based on the physiological attribute of the patient; transmitting the set of programming instructions from the programming module to the communication module; and transmitting stimulation energy from the communication module to the first pulse generator based on the set of programming instructions.

In certain embodiments, the method further comprises: determining an alignment of the pulse generator coil and the communication coil; and modifying at least one of the programming instructions and the stimulation energy transmission based on the alignment of the pulse generator coil and the communication coil. In particular embodiments, the method further comprises: ramping the stimulation energy to a first stimulation level, the first stimulation level being an increment of a stimulation goal; and ramping the stimulation energy to a subsequent stimulation level, the subsequent stimulation level being another increment of the stimulation goal, wherein the subsequent stimulation level varies from the first stimulation level by at least one of stimulation amplitude, frequency, pulse width, and duration.

Specific embodiments further comprise selecting a specific branch of the hypoglossal nerve on which to place the first pulse generator. In certain embodiments, selecting the specific branch of the hypoglossal nerve on which to place the first pulse generator comprises: placing the first pulse generator on a first branch of the hypoglossal nerve; transmitting stimulation energy to the first pulse generator; and observing a response from the patient. In particular embodiments, the response from the patient is a recoil of a tongue.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximate" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 1A is a drawing of a Smart Wireless Implantable Pulse Generator or SWIPG or IPG secured in a carrier according to an example;

FIG. 1B is a drawing of an IPG implanted and secured to the hypoglossal nerve by the carrier according to an example;

FIG. 1C is a drawing of patient wearing a smart pillow or hub configured to communicate with the implanted IPG according to an example;

FIG. 1F is a table showing different system components according to an example;

FIG. 6 is an example of the application according to an example;

DETAILED DESCRIPTION OF ILLUSTRATIVE EMBODIMENTS

Figure 1D:
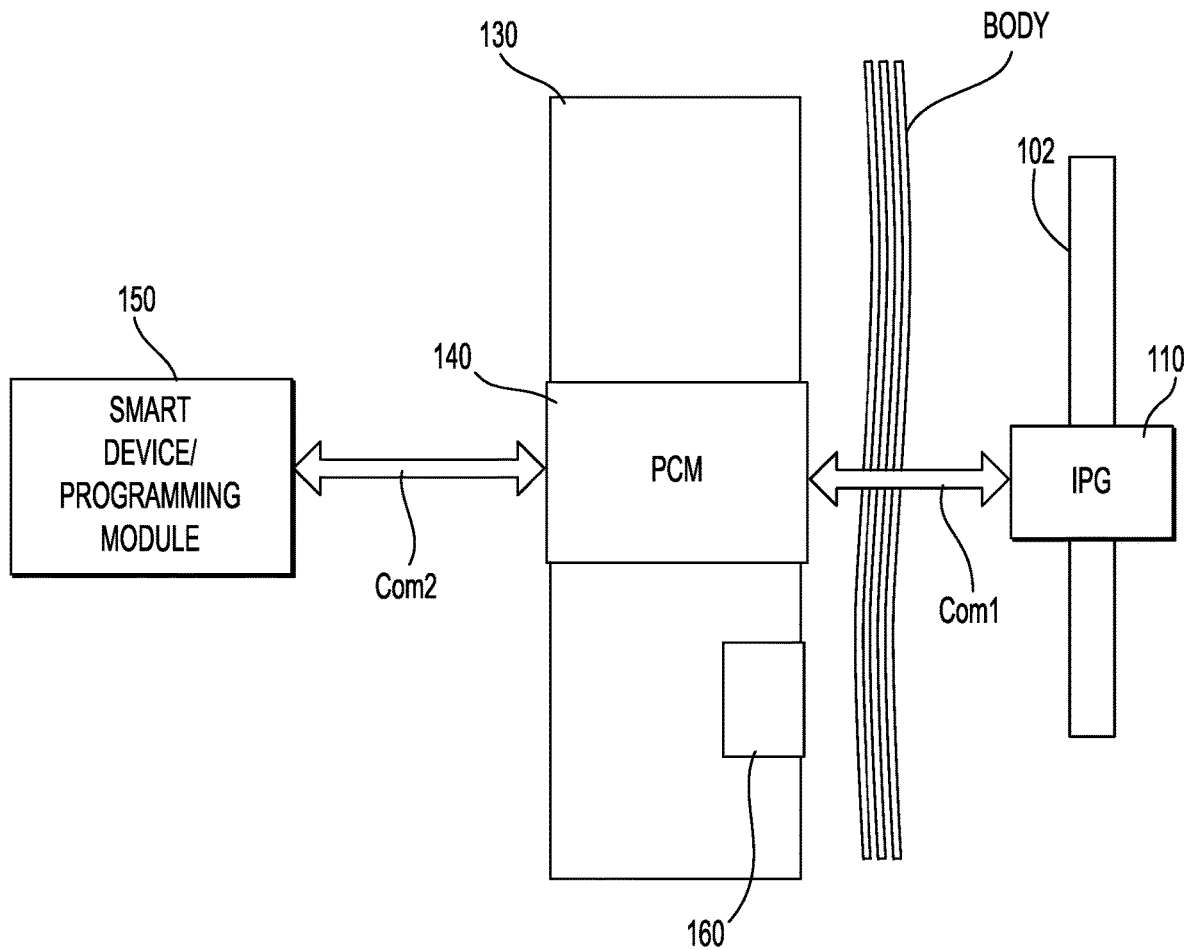
FIG. 1D is a drawing of components of the system interacting according to an example.
Figure 1E:
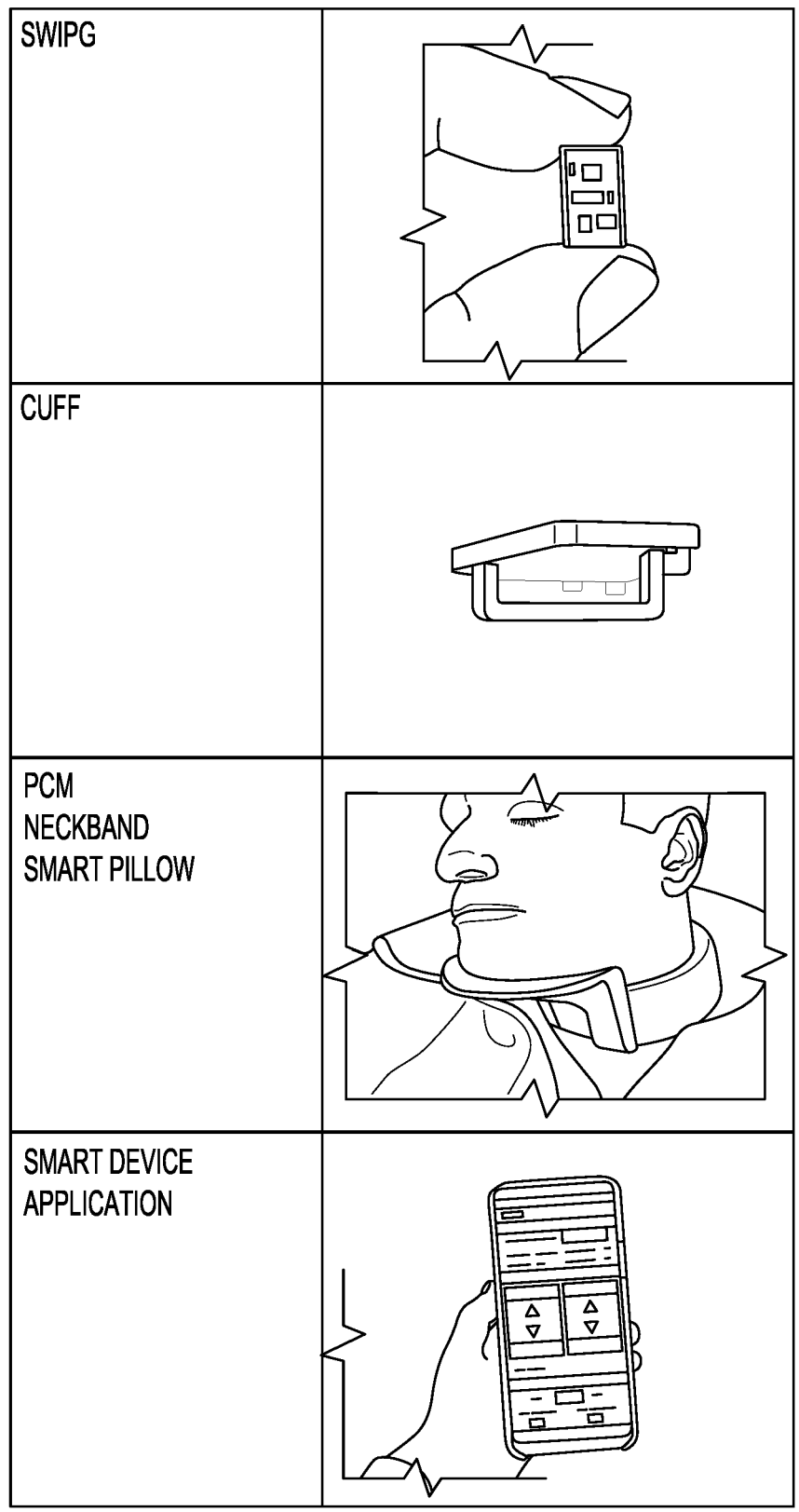
FIG. 1E is a table showing different components of the system including the IPG, the carrier, the hub housing a power and communication module (PCM), and a programming module application according to an example.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Figure 7A:
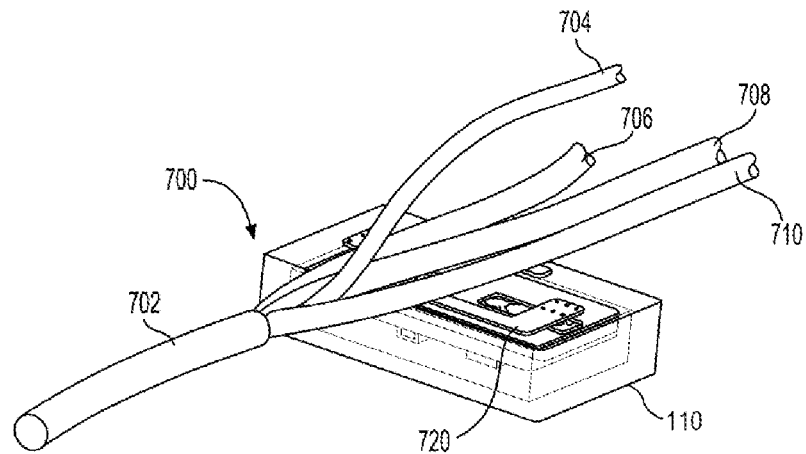
FIGS. 7A-C are drawings of the IPG having electrode leads positioned relative to branches of the hypoglossal nerve according to an example.
Figure 7B:
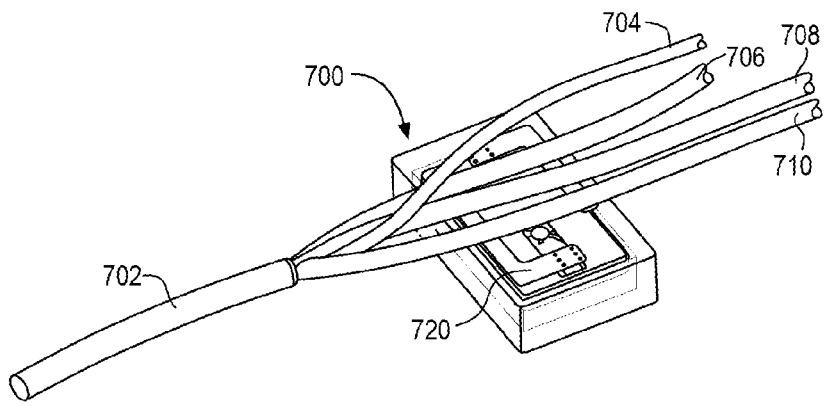
Figure 7C:
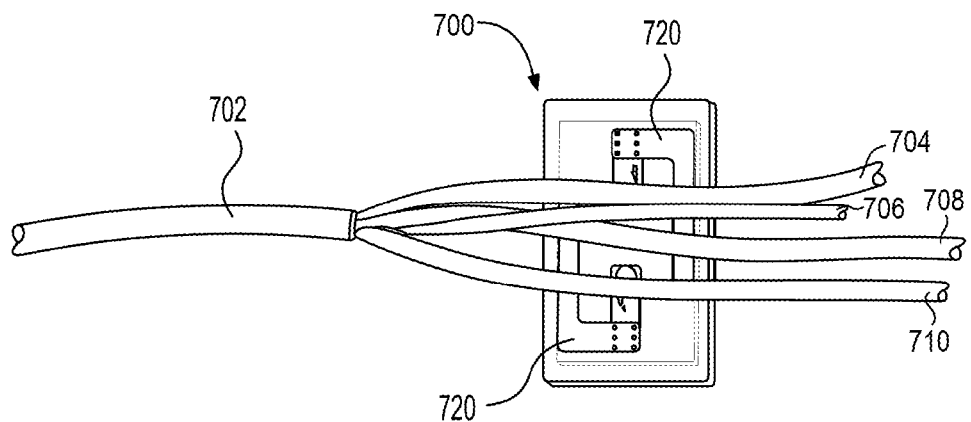

As shown in FIGS. 1A-1C, in an exemplary embodiment, the ReVive system includes at least one Smart Wireless Implantable Pulse Generator, SWIPG or IPG 110, a carrier 120 configured to hold the IPG to the nerve of interest 102, and a smart pillow or hub 130 configured to position a Power and Communication Module (PCM) 140 in relation to the IPG, and a smart device or programming module 150 configured to program the PCM. In the embodiment shown in FIG. 1A, IPG 110 is positioned approximately perpendicular to nerve 102, which in this specific embodiment is a hypoglossal nerve. A more detailed view of such a configuration is shown in FIGS. 7A-7C, which show branches 704, 706 and 708 of nerve 702 extending across the longer sides of IPG 700 and electrodes 720. In other embodiments, it may be preferable to align IPG 110 such that IPG 110 is positioned approximately parallel with the nerve of interest. For example, as shown in FIG. 1G, IPG 110 is positioned approximately parallel with nerve 102 of a patient 100, which in this embodiment is a vagus nerve. In such an embodiment, the nerve or nerves of interest are positioned approximately perpendicular to the nerves shown in FIG. 7C, such that the nerve(s) of interest are substantially aligned with the longer sides of the IPG as well as the electrodes.

Figure 1G:
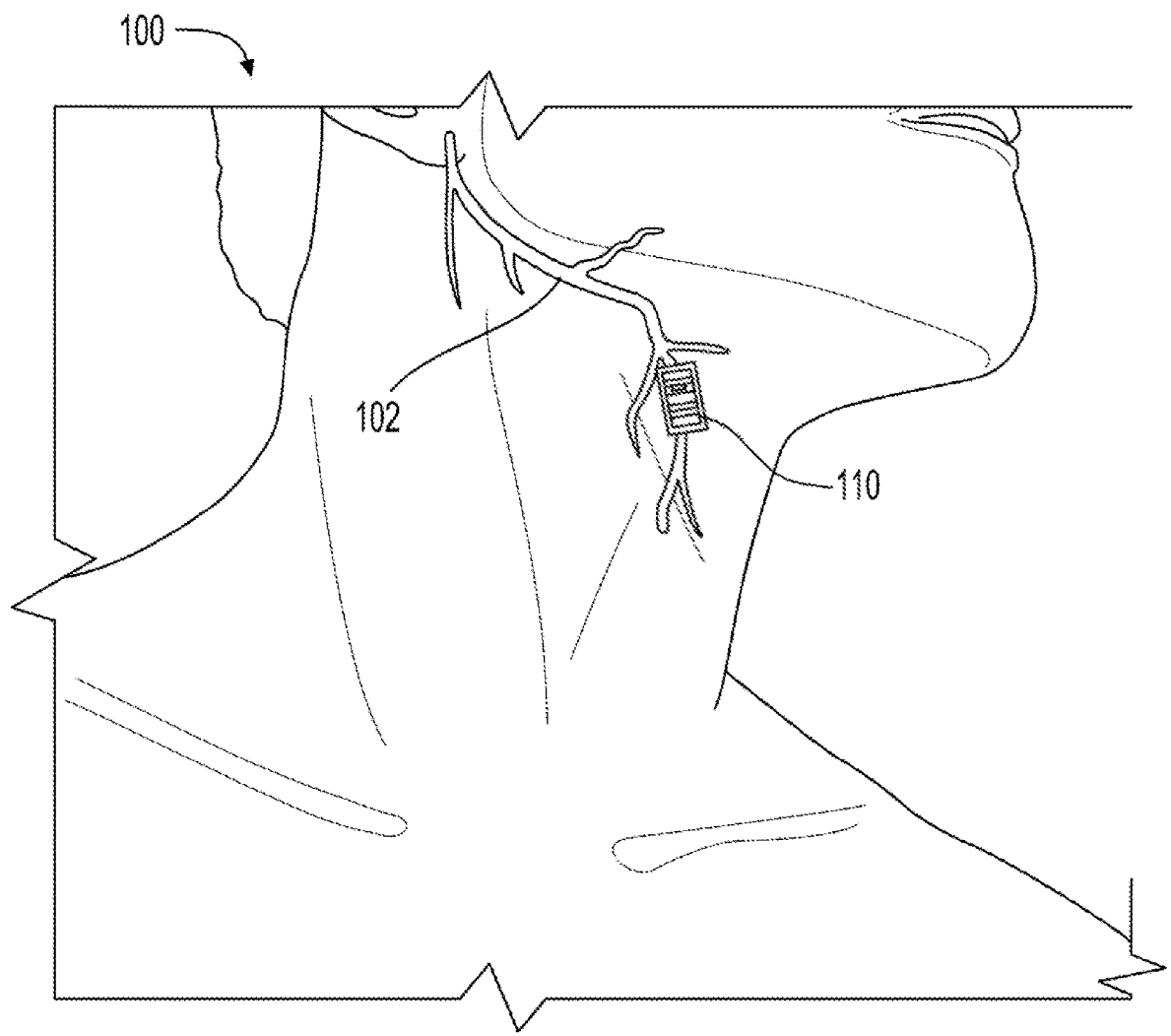
FIG. 1G is a drawing of a Smart Wireless Implantable Pulse Generator or SWIPG or IPG secured in a carrier according to an example.
Figure 3A:
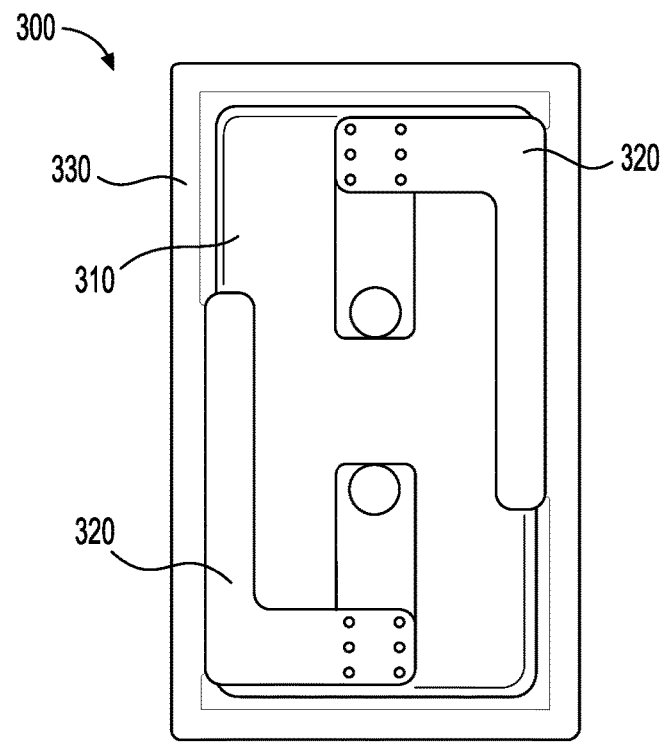
FIGS. 3A-3D are drawings of an IPG according to an example.
Figure 3B:
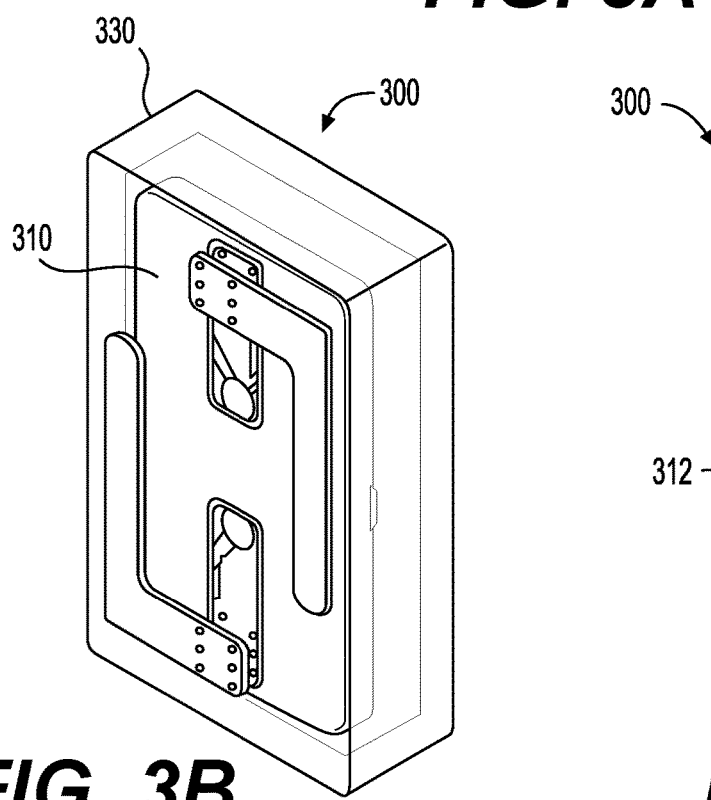
Figure 3C:
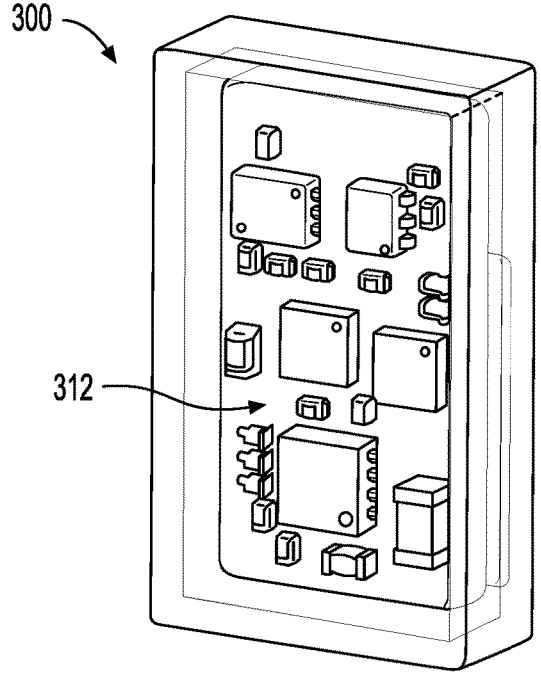
Figure 3D:
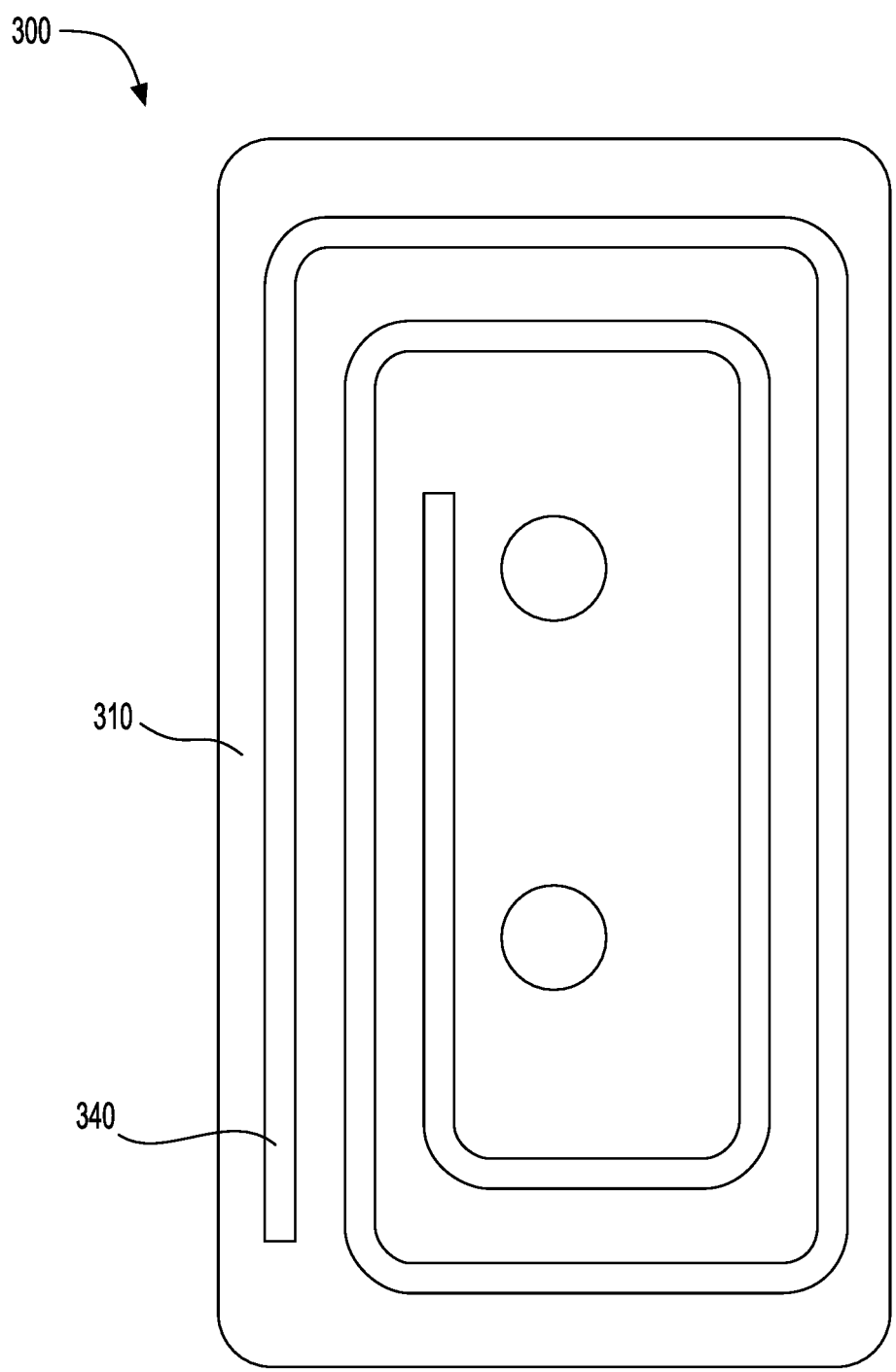

FIG. 1D is a drawing of components of the system interacting according to an example. In some implementations, the system includes the implantable pulse generator, the PCM, and the programming module. The IPG is implanted directly on the nerve of interest 102 and delivers electrical stimulation through electrodes exposed on its enclosure. The PCM remains outside the body and is in communication with a coil positioned relative to the IPG during activation, such as stimulation and programming. In an example, the hub 130 is configured to position a PCM coil of the PCM in relation to an IPG coil of the IPG, as shown in FIG. 3D.

In an example, the programming module 150 controls the IPG 110 via the PCM 140 to set (e.g. define and/or adjust) stimulation energy attributes parameters and trigger stimulation. The programming module communicates with the PCM using Bluetooth Low Energy (BLE). In an example, the PCM is battery powered and provides wireless power to the IPG through inductive coupling at a frequency that results in negligible absorption in the body. In an example, the frequency is around 13.56 MHz. In an example, the PCM communicates with the IPG via Near Field Communication (NFC).

The IPG coil is used to harvest power from an oscillating magnetic field, and to enable communication with external devices by modulating this field. The coil is integrated into the PCB as metal traces. Metal layers 2, 3, and 4 contain 3 coil turns each, while layer 1 (top layer) has a single partial turn. The coil occupies the periphery of each layer to maximize the total amount of magnetic flux through the coil. The trace width and spacing between traces are both 8 mil. The inductance of the coil is 970 nH. The use of a ground plane is avoided entirely to reduce eddy current losses in the coil, and is avoidable due to the close proximity of the surface mounted components and lack of long traces between components.

In an example, the IPG communicates to the PCM via NFC (Com1). In an example, the PCM communicates to the programming module via Bluetooth (Com2).

In an exemplary embodiment of the ReVive system typical operation, the patient is implanted with at least one IPG on each hypoglossal nerve using a carrier to hold the IPG or implant on the nerve. A PCM is placed inside the hub which is worn around the patient's neck during sleep. The hub is configured to position the PCM's coil under the patient's chin. The PCM coil can be deformable and adapted to a shape of the hub or patient body. In some implementations, the hub is also configured to position a pulse oximeter against the patient's neck. The PCM powers the IPG and communicates with a programming module (e.g., smart mobile device or tablet) running an application. In some implementations, the PCM coil or hub coil can include a cooling feature as to compensate for heat transmitted to the patient's body. Examples of cooling features include materials to draw heat away from the surface of the skin, active coolers providing cooling, and electrical stimulation or a slow release of an agent configured to open skin pores on the patient's skin to allow for natural sweat glands to cool the skin.

At bedtime the patient puts the smart pillow around their neck and turns it on. Using the ReVive application on their smart device, if necessary, they connect via Bluetooth to the smart pillow and set the current comfort level for each IPG and a sleep delay. They can verify that the PCM is communicating with the IPGs and test the comfort level. When they have set up the ReVive system for the night, they turn on the sleep delay and go to bed. After the end of the delay the programming module will communicate with the PCM to power the IPGs.

In some implementations, the system operates in an open loop. In an exemplary embodiment, stimulation is based on the typical respiration rate of the patient as measured in the sleep study and is set by the clinician. The clinician can set a range of respiration rates and stimulation duty cycles not to exceed 50%. For example, if the clinician sets the ReVive system to stimulate 15 times per minute and 50% duty cycle, the ReVive system will stimulate the hypoglossal nerve every 4 seconds for 2 seconds, which is configured to move the tongue and open the airway. The clinician can set the respiration rate range from 12 to 20 times per minute. In some implementations, the patient may adjust the setting manually using buttons on the hub or PCM. The system can be configured to automatically adjust the settings based on one or more biosignals collected.

In an aspect, the hub and/or PCM can be configured to record and/or receive EEG signals. In an example, the K-complex which is associated with brief awakenings can be monitored for within the EEG signals.

Figure 2:
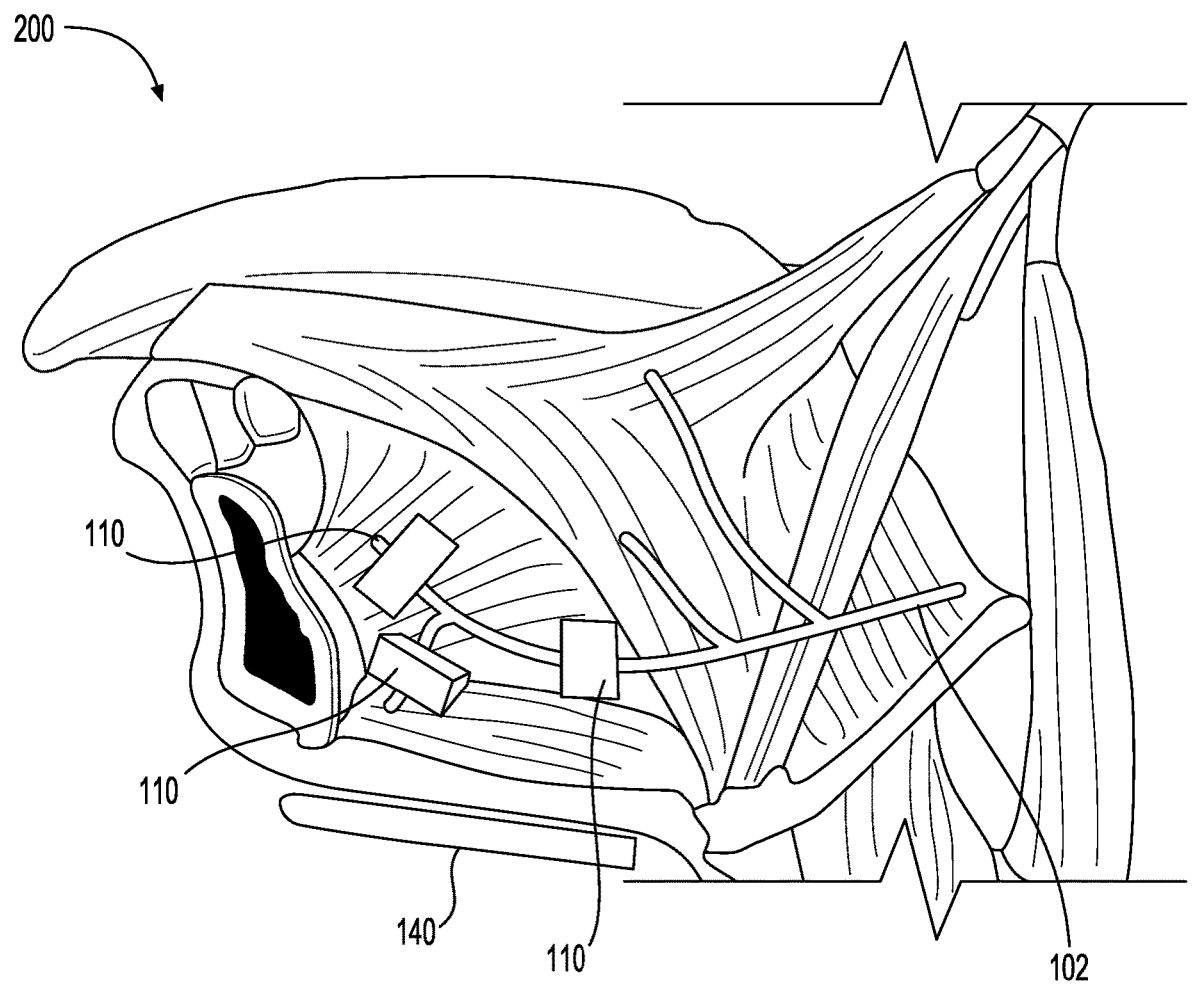
FIG. 2 is a drawing of multiple IPGs implanted and secured to different branches of the hypoglossal nerve according to an example.

Turning to FIG. 2, multiple IPGs 110 may be implanted and secured to different branches of the hypoglossal nerve and configured to control movement of a patient's tongue 200 according to an example. Each IPG can be independently controlled or configured to work synchronously. In an example, two or more IPGs can communicate with each other to coordinate stimulation to a nerve or communication with the PCM. In an example, two or more IPGs can be connected with a cable or wire to communicate power or information. Connected IPGs can serve as a master and a slave. In an example, a master IPG can be configured to communicate between the PCM and a slave IPG.

Figure 5A:
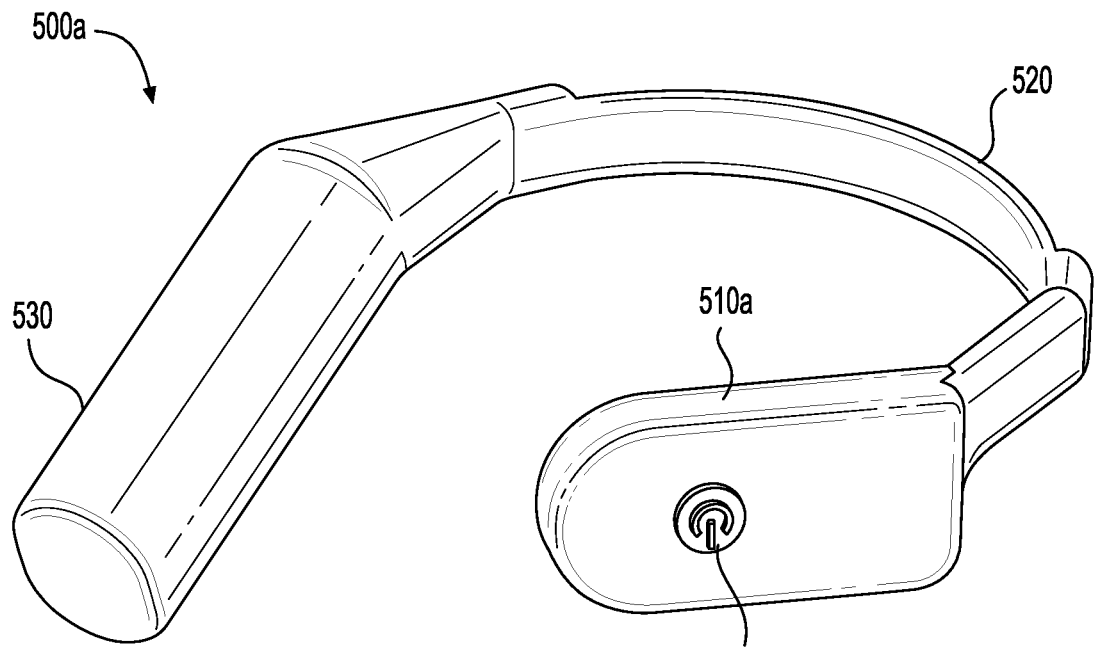
FIG. 5A is a drawing of a PCM including a controller, a neckband, and a power source according to an example.
Figure 5B:
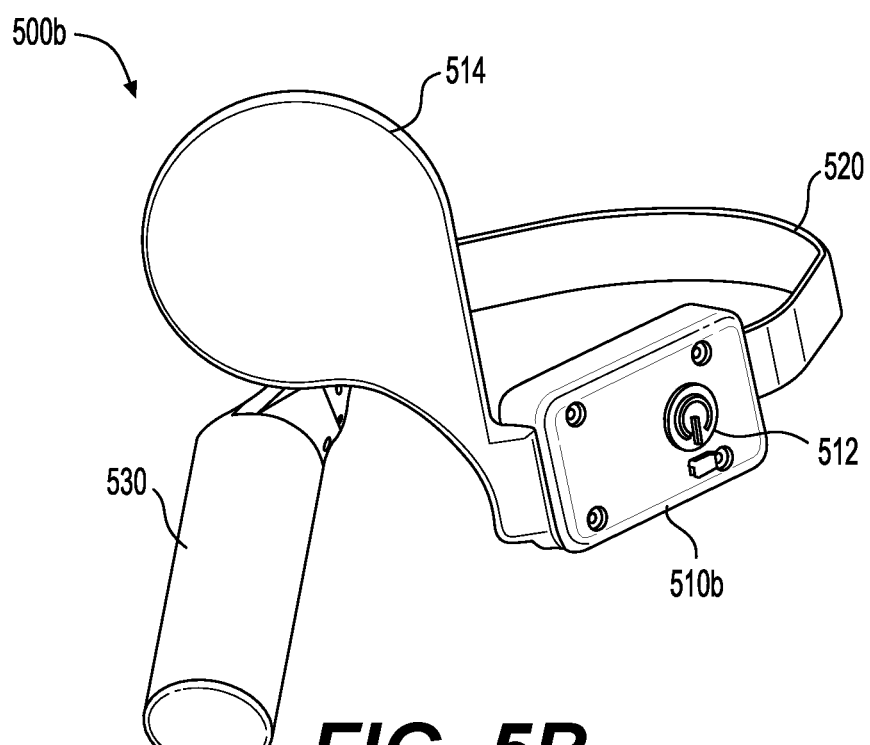
FIG. 5B is a drawing of a PCM including a controller having a PCM coil, a neckband, and a power source according to an example.

Turning to FIGS. 5A-5B, a PCM 500a-b generally includes a controller 510a-b having a button 512, a neckband 520, and a power source 530 according to an example. As shown in FIG. 5A, the PCM 500a can include a controller 510b configured to utilize a coil within the hub to communicate with and control the IPGs. As shown in FIG. 5B, a PCM 500b can include a controller 510b having a PCM coil 514 according to an example.

In an aspect, the power source 530 can be function as a counterweight to the controller and maintain positioning of the PCM around the neck of the patient. The power source 530 can open and use a replaceable battery or remained hermetically sealed and use a rechargeable battery which can be recharged wirelessly or by a wired port. In one configuration the coil could go around the chin with straps attached around the head and neck to hold it in place during sleep. In another configuration there could be a chin strap with the coil attached and position under the chin with straps holding the coil in place by going around the head and neck.

In an aspect, the power and communication module (PCM) includes a protocol configured to allow communication with a single IPG at a time. The PCM is designed with a single coil. In an example, the PCM coil is configured to be soft flexible as to conform to the shape of the patient or the hub. The coil can have different shapes and sizes. For example, the coil can have a 6 cm diameter circular shape or a 55 mm×70 mm oval shaped coil.

In an example, the PCM is designed to pair with a single IPG. In an example, the hub and PCM can have one or more coils that work cooperatively together. In an example, the hub can have a coil configured to be connected to the PCM and used to communicate with one or more IPGs. In another example, the hub and PCM may include multiple coils configured to be used with multiple IPGs. In another example, the hub and PCM may include multiple coils configured to be used with one or more IPGs, where an optimal coil will be used from either the PCM or hub when aligned with each IPG. The PCM is configured to power both a contra and ipsilateral IPG.

In some implementations, the PCM includes one or more biosensors 160 configured for monitoring a range of biosignals including at least one of but not exclusively, heart rate, oxygen saturation, sleep sounds, patient movement, eye movement, and electrical activity of the brain and eye. In an example, the PCM includes one or more pulse oximeters, one or more microphones, accelerometers, and electroencephalograms (EEGs).

Prior to sleep, the patient places the PCM around their neck and turns it on. As the patient moves around prior to sleep or between sleeping epochs at night at least one of the biosignals and accelerometers detect that the patient is vertical and moving around and could stop or alter stimulation of the hypoglossal nerve.

The IPG is configured to receive power from the PCM and deliver targeted electrical stimulation to the nerve of interest. The IPG is configured to be positioned relative to branches of the hypoglossal nerve according to an example. The IPG is implanted directly on the nerve of interest and delivers electrical stimulation through electrodes exposed on its enclosure. In some implementations, the IPG includes at least a pair of electrodes, a printed circuit board (PCB) 310, and an IPG coil 340 as shown in FIG. 3D. As shown in FIGS. 3A and 3B, an IPG 300 can be glass encapsulated 330 have elongated electrodes 320 according to an example. FIG. 3C illustrates control components 312 of PCB 310 (labeled in FIG. 3B). In an example, the electrodes 320 can be slightly elevated from the PCB as to extrude from the glass encapsulation. In some implementations, the leads can be segmented and allow for selective anodic blocking of the nerve.

In some implementations, the IPG can be functionally similar to the ReStore Stimulator as described in a publication titled "ReStore: a wireless peripheral nerve stimulation system" published in Journal of Neuroscience Methods on May 15, 2019 herein incorporated by reference in its entirety. In an aspect, the IPG is configured to be minimally sized. In an example, the IPG size is about 0.3 CC.

In an example, the IPG is configured to prevent DC current. In an example, the IPG includes a current limiting capacitor to stop DC current, as well as has a maximum of 1.2 mA and 10 Volts. In some implementations, the IPG processor has Ferroelectric Memory (FRAM) to ensure unlimited read write cycles. In an example, the IPG processor is configured to have an embedded code base. The embedded code allows the device to store programs and run independent of communication with the externals.

In an example, the IPG is configured to communicate with the PCM using a backscatter technique. The IPG firmware stores stimulation parameters including one or more of current amplitude, pulse width, pulse frequency, specified waveform shapes including current amplitude, rise time and fall time. The IPG firmware is configured to have a sham mode that allows the system to step down current from some value to zero milliamps to blind the control arm of clinical trials. In an aspect, the IPG firmware is configured to permit communication with multiple IPGs. In an example, the IPG firmware is configured to sustain stimulation with minimal communication with the PCM. In an example, the IPG firmware is configured to allow a slow increase in current to allow for accommodation as the patient falls asleep slowly ramping up to increase efficacy.

The IPG includes a low power microcontroller (MCU) configured to handle application-level communication and has a digital to analog converter that is used to control the pulse amplitude. In an example, the MCU can be 8-bit such as part number EFM8SB1 from Silicon Labs (Austin, TX). In an aspect, the MCU controls the switches to deliver pulses of desired duration and frequency. Charge balancing is achieved by changing the direction of flow of current by alternating the electrode through which the charge is delivered. At the end of the pulse, the electrodes can be shorted together to discharge them completely.

In some implementations, the IPG can use an NFC tag integrated circuit (IC) to perform wireless communication and power harvesting. In an example, the IPG includes a power harvesting circuit configured to outputs a voltage which is used to power the rest of the device. In an example, the voltage can have a maximum of 3V. The output from the NFC IC can be stepped-up to 10V by a boost in order to drive stimulation current through high tissue impedances. An example of a boost converter is part number: LT8410 from Linear Technology (Milpitas, CA). The IPG can include a stimulation circuit which includes an op amp that amplifies the analog output range of the MCU to 0-1200 μA. An example of a stimulation circuit op amp is part number: OPA170 from Texas Instruments (Dallas, TX). The output of the op amp is connected to the electrodes via two single pole double throw switches. An example of an op amp is made by Vishay (Malvern, PA).

Figure 8A:
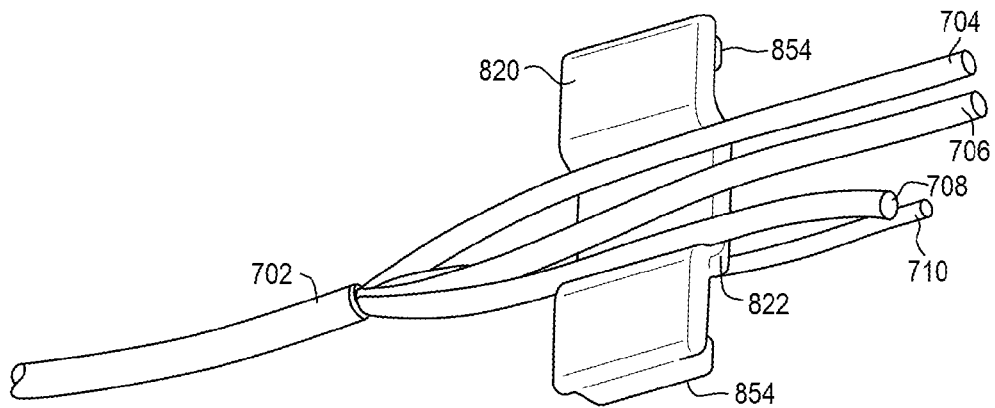
FIGS. 8A-C are drawings of the carrier positioned relative to branches of the hypoglossal nerve and isolating at least one branch of the hypoglossal nerve according to an example.
Figure 8B:
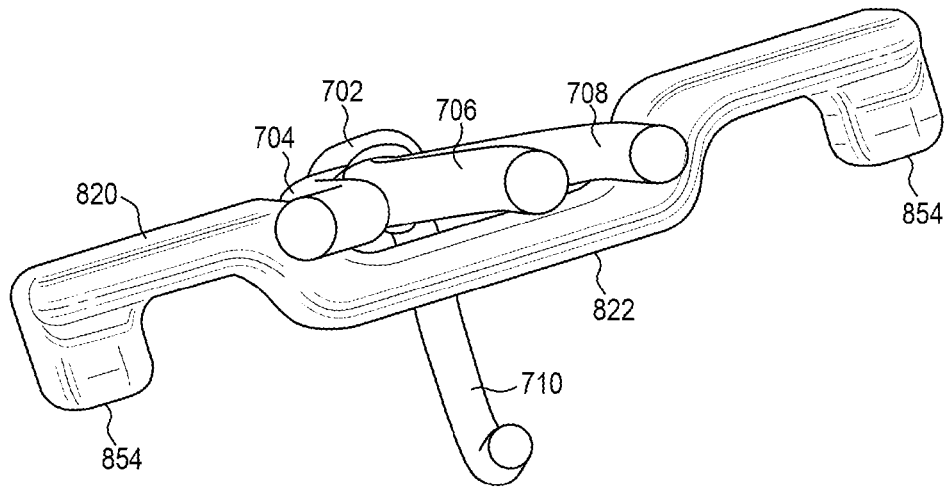
Figure 8C:
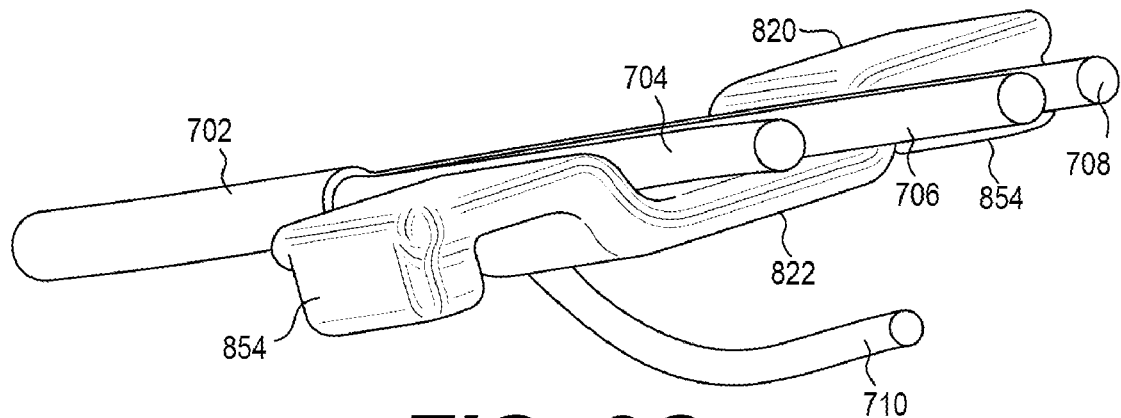

In some implementations, it may be beneficial to isolate one or more branches of the hypoglossal nerve. FIGS. 7A-7C show placement of an IPG 700 having at least two electrode leads 720 positioned relative to branches 704-710 of the hypoglossal nerve 702 according to an example. At least one branch of the hypoglossal nerve can be isolated using a carrier such as shown in FIGS. 8A-8C. In an example, a cuff 820 comprising securement members 854 and a strap portion 822 can be used to secure branches 704, 706 and 708 of hypoglossal nerve 702 while excluding branch 710 of hypoglossal nerve 702. In an example, the cuff can have a spiral shape wrapping the nerve.

Figure 9A:
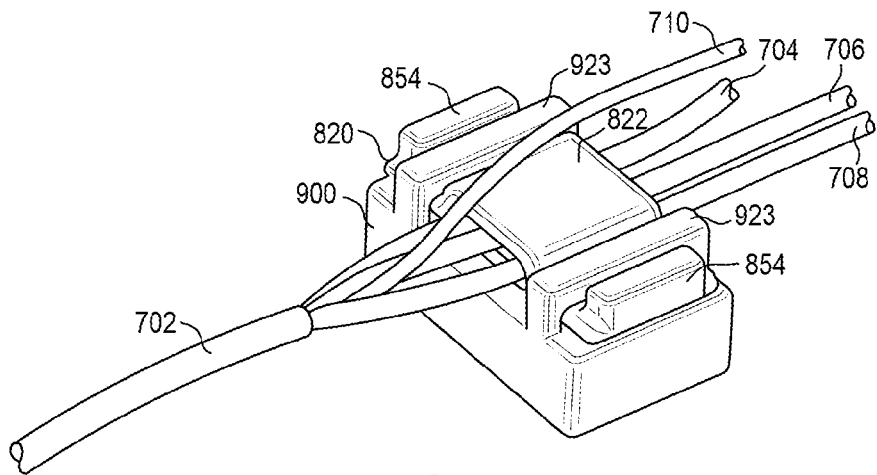
FIGS. 9A-C are drawings of the carrier secured to the IPG positioned relative to branches of the hypoglossal nerve, where at least one branch of the hypoglossal nerve is isolated from the IPG according to an example.
Figure 9B:
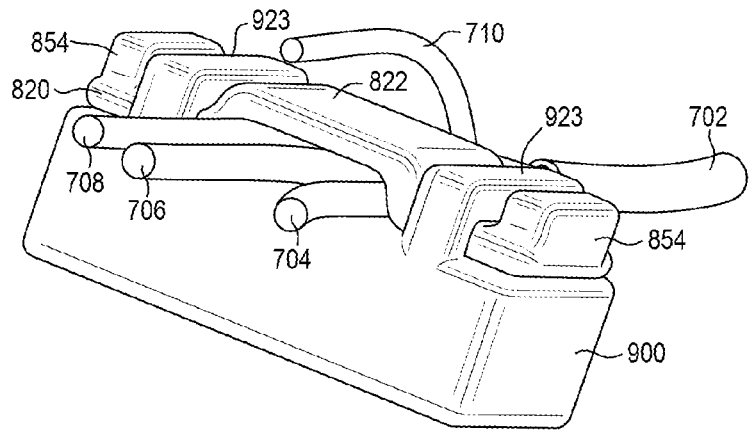
Figure 9C:
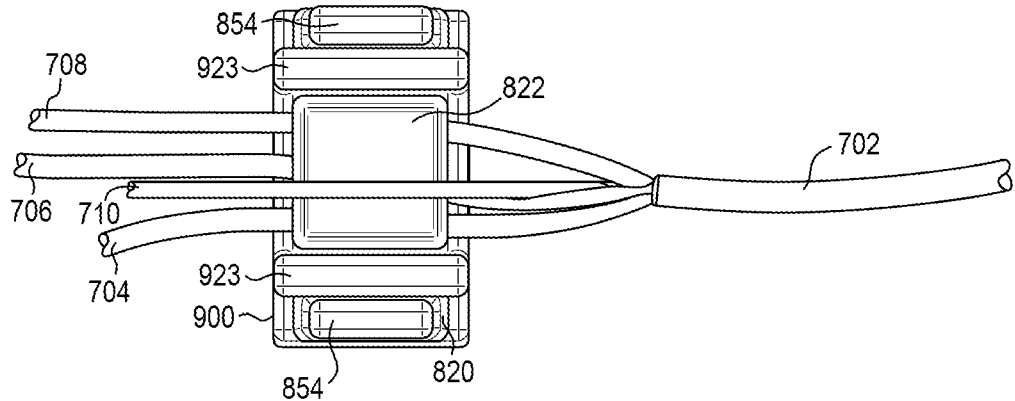

As shown in FIGS. 9A-9C, a securement member 854 at each end of cuff 820 can be inserted into a corresponding retention member 923 of a carrier 900 containing an IPG (not visible in the figures). In exemplary embodiments, cuff 820 and carrier 900 can be positioned relative to branches of the hypoglossal nerve, where at least one branch of the hypoglossal nerve is isolated from the IPG according to an example. In one embodiment, a securement member 854 at one end of cuff 820 can be initially inserted into a retention member 923 on carrier 900. The branches that are selected for stimulation from the IPG are then placed between carrier 900 and cuff 820, and cuff 820 is placed over the selected branches (e.g. branches 704, 706 and 708 in FIGS. 9A-9C). Securement member 854 (at the opposing end of cuff 820 from the securement member already secured to carrier 900) is then secured into the remaining retention member 923.

In particular embodiments, carrier 900 and the IPG are separable, and in other embodiments, the IPG may be integral with carrier 900. In an example, the IPG can include retention members 923 formed from the glass encapsulation. In certain embodiments, selection of the specific branch of hypoglossal nerve 702 on which to secure carrier 900 can comprise placing carrier 900 on a first branch of hypoglossal nerve 702, transmitting stimulation energy to the IPG contained within carrier 900, and observing a response from the patient. Specific patient responses may include a recoil of the tongue, for example.

Figure 9D:
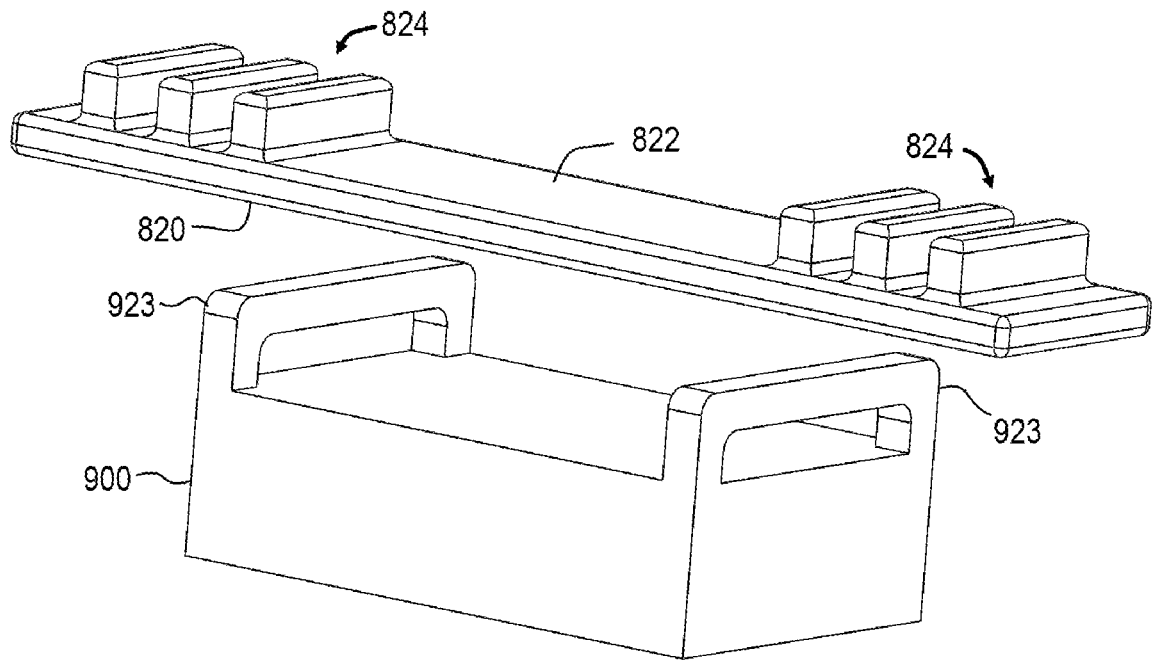
FIGS. 9D-9E are perspective and front orthogonal drawings of a separate cuff and carrier prior to securement to a hypoglossal nerve.
Figure 9E:
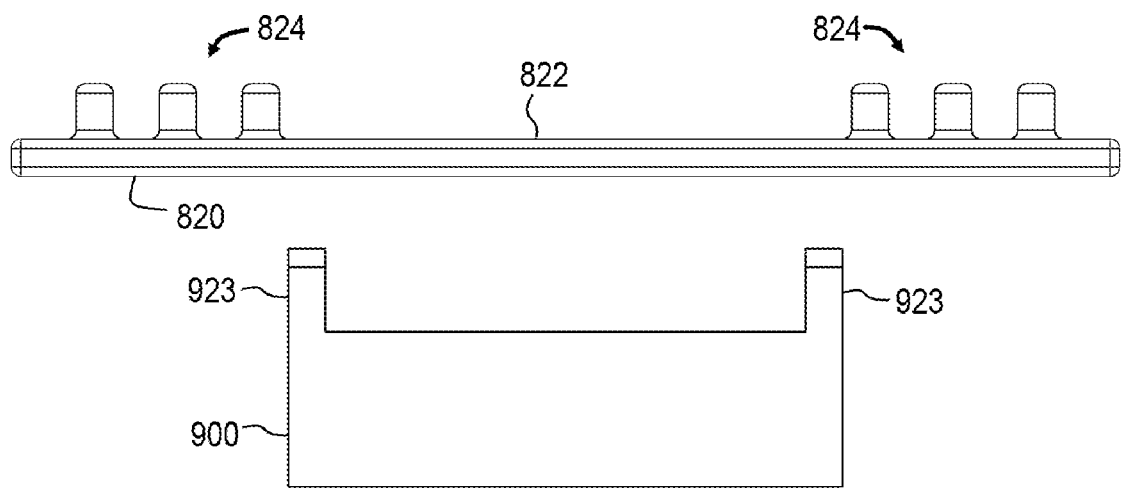

FIGS. 9D and 9E show perspective and front orthogonal views, respectively of cuff 820 separated from carrier 900 and retention members 923. In this embodiment, cuff 820 comprises a plurality of adjustment members 824 proximal to each end of cuff 820. Cuff 820 further comprises a central strap portion 822 between adjustment members 824. This embodiment is secured to the nerve branches selected for stimulation in a manner similar to the embodiment shown and described in FIGS. 9A-9C, but also provides the ability to adjust the length of cuff 820 secured between retention members 923. This adjustment capability can allow the user to secure carrier 900 to the selected nerve branch or branches without adversely compressing the nerve or nerve branches (as discussed in further detail herein).

In this embodiment adjustment members 824 proximal to one end of cuff 820 can be inserted into a first retention member 923 similar to the embodiment described in FIGS. 9A-9B. The selected nerves can then be placed between cuff 820 and carrier 900, and the remaining adjustment members 824 at the free end of cuff 820 (e.g. the end of cuff 820 not secured to carrier 900) can then be inserted into the opposing retention member 923. One or more ends of cuff 820 can then be pulled away from carrier 900 so that the desired amount of compression is placed on the nerve branch or branches secured between carrier 900 and cuff 820. In certain embodiments, portions of cuff 820 extending beyond retention members 923 can be trimmed to reduce the length of cuff 820 after the nerve or nerve branches have been secured.

Similar to the embodiments described in further detail below, strap portion 822, adjustment members 824 and/or retention members 923 may comprise structural features to provide additional flexibility of cuff 820 and carrier 900 in order to avoid adversely compressing the nerve or nerve branches. For example, central strap portion 822 may comprise a reduced thickness portion. In addition, adjustment members 824 and/or retention members 923 can be flexible and capable of deformation when carrier 900 is secured to a nerve or nerve branches by strap 822. Carrier 900 further comprises one or more apertures (not shown) proximal to electrodes of IPG similar as apertures 1027 shown in FIG. 10A. In case of the IPG comprising retention members 923, the IPG can include one or more spacers between electrodes for purposes described below. In an example, the spacer(s) can be made from the glass encapsulation or from another material that is assembled with the IPG.

Figure 10A:
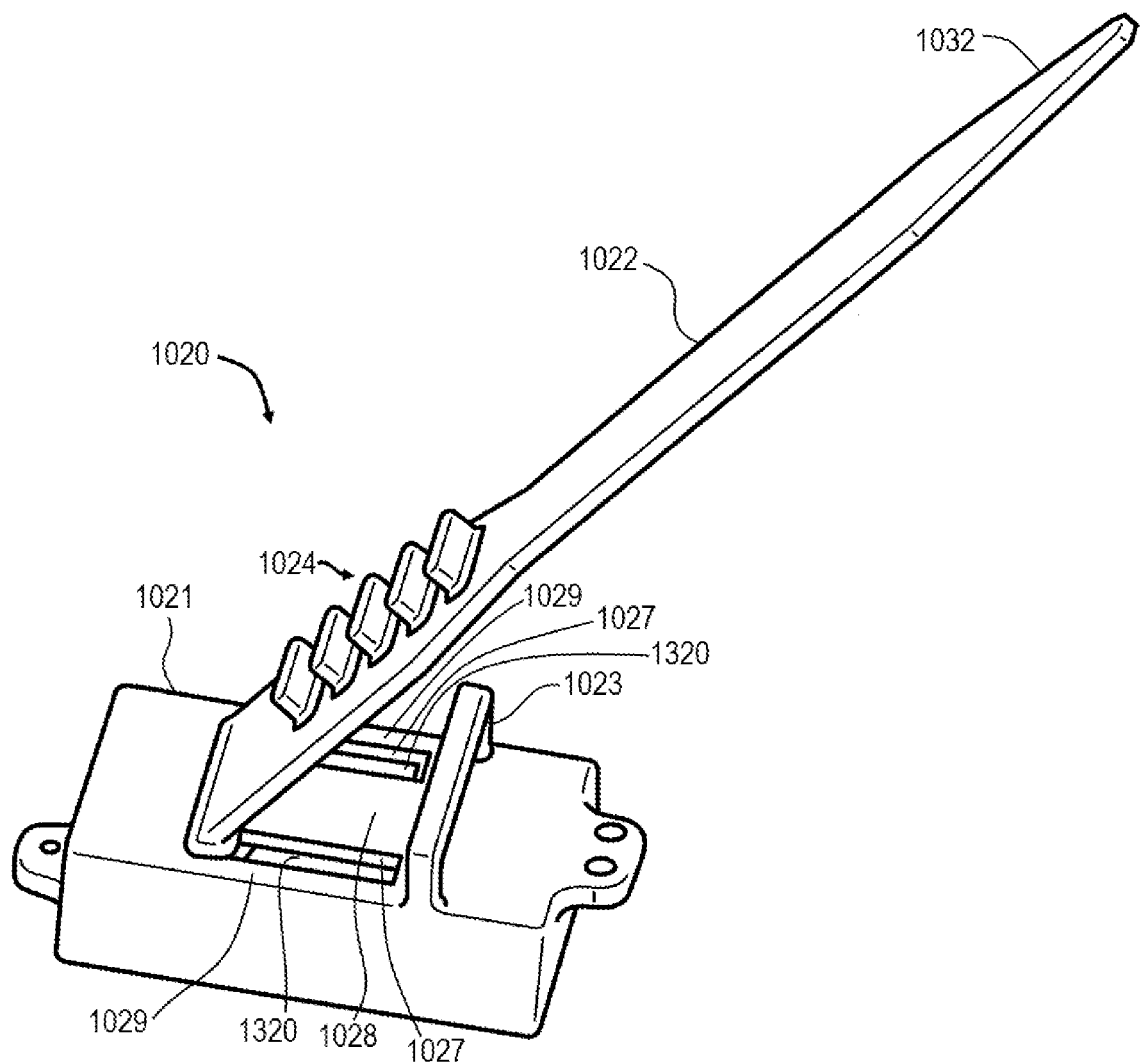
FIGS. 10A-10H are perspective and section drawings of a carrier including a retention member and a strap with adjustment members configured to secure around a nerve according to an example.
Figure 10B:
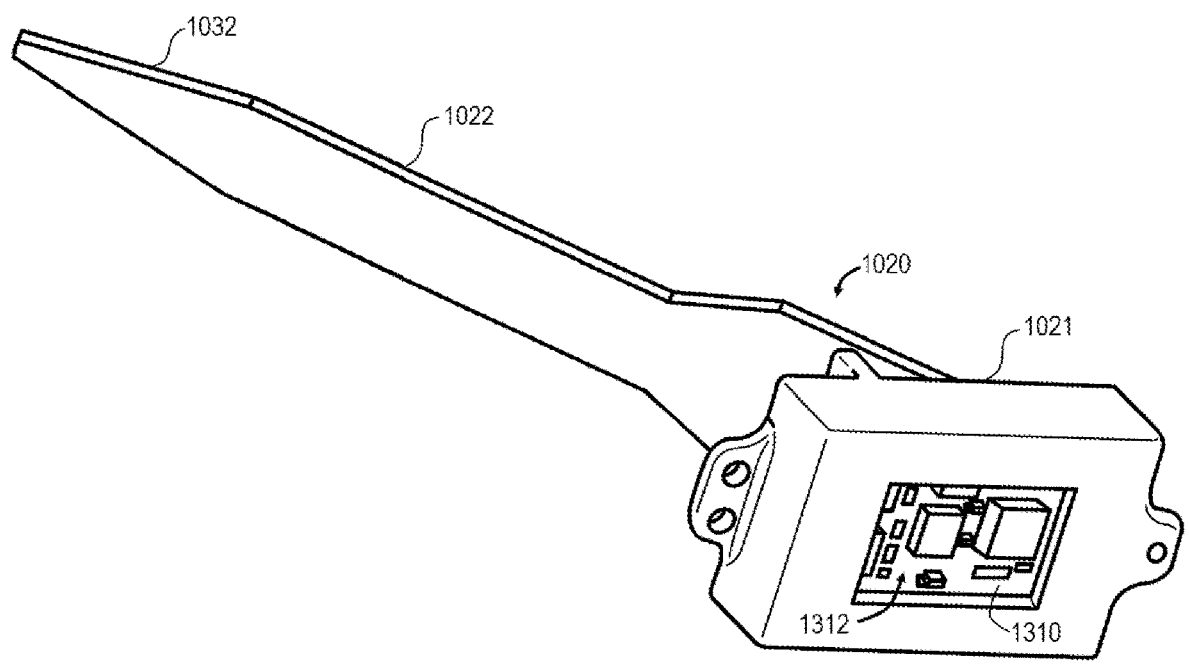
Figure 10C:
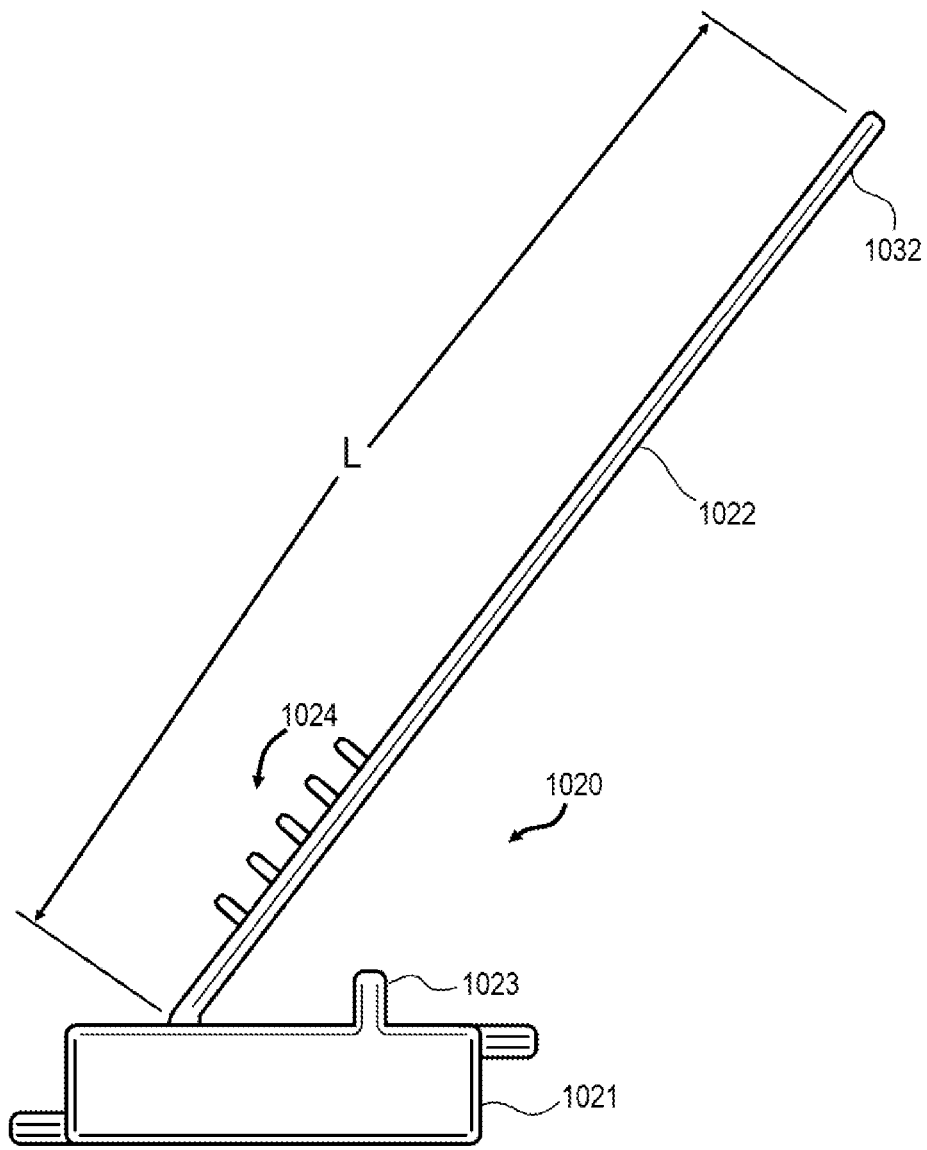

FIGS. 10A-10G illustrate an embodiment of a carrier 1020 according to the present disclosure. For purposes of clarity, not all features are labeled with reference numbers in each view. FIGS. 10A-10C illustrate perspective and side view of carrier 1020. FIGS. 10D-10G illustrate perspective and section views of carrier 1020 secured to a hypoglossal nerve 1002, and FIG. 10H illustrates a section view of carrier 1020 secured to hypoglossal nerve branches 1004, 1006 and 1008 while excluding branches 1003 and 1005.

In the embodiment shown, carrier 1020 comprises a housing 1021 with a retention member 1023 and strap 1022 with adjustment members 1024 configured to engage retention member 1023. In particular embodiments, strap 1022 comprises an end 1032 that is tapered to allow for easier insertion into retention member 1023. In the embodiment shown, PCB 1310 is located within housing 1021 and comprises control components 1312.

Figure 10D:
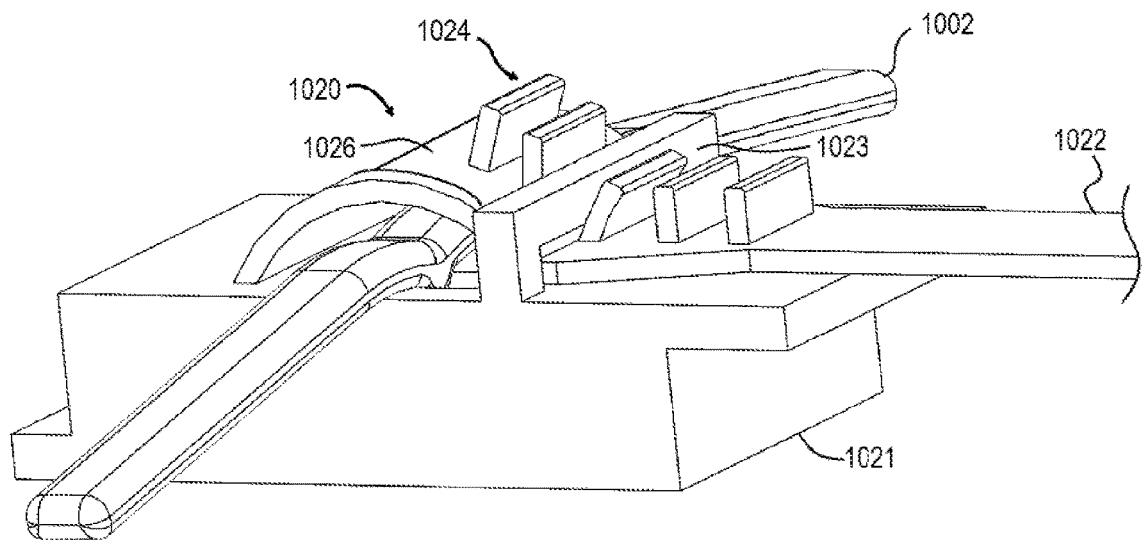
Figure 10E:
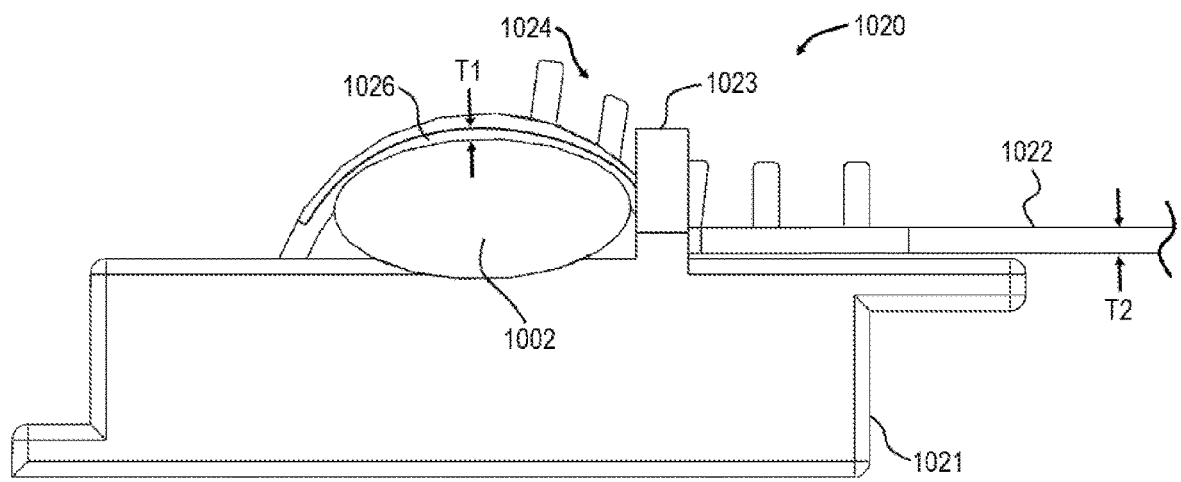
Figure 10F:
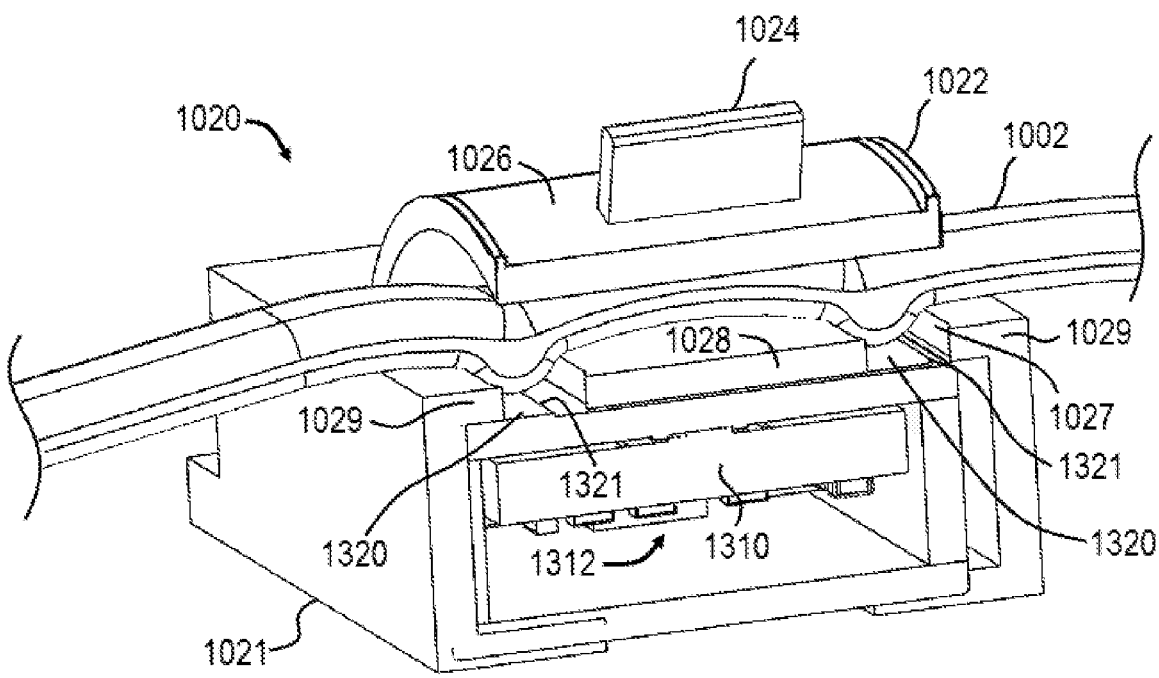
Figure 10G:
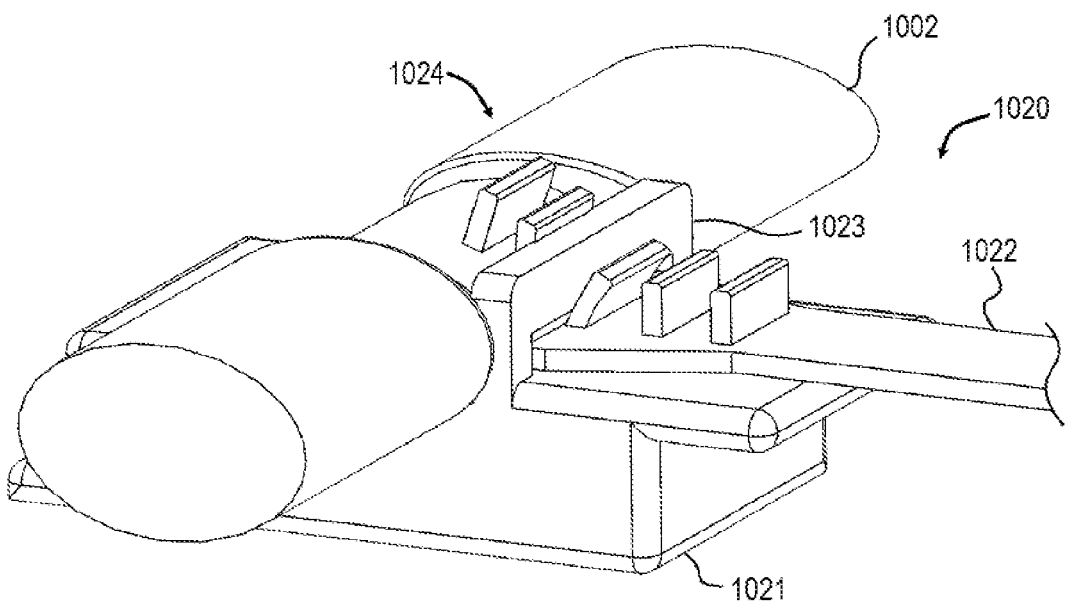
Figure 10H:
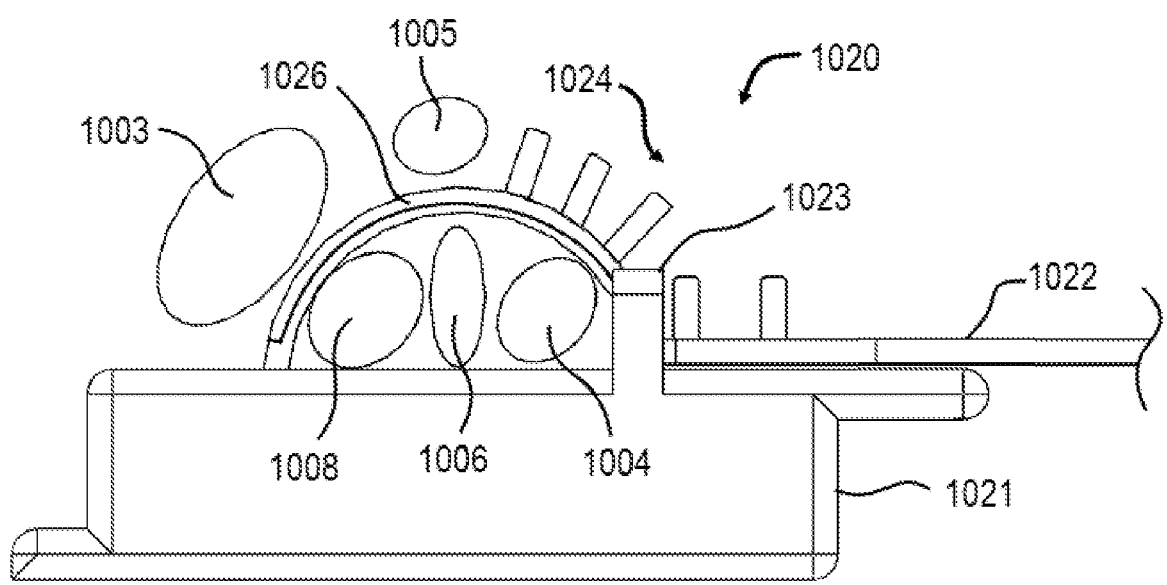

During use, carrier 1020 can position an IPG 1010 proximal to a nerve 1002 (e.g. a hypoglossal nerve) or multiple nerve branches 1004, 1006 and 1008 as shown in FIG. 10H. Strap 1022 is configured to be of sufficient length L (shown in FIG. 10C) to allow strap 1022 to extend over one or more nerves and through retention member 1023 such that adjustment members 1024 engage retention member 1023 while a medical professional (e.g. surgeon) grasps end 1032 ex vivo (e.g. outside of the implantation location of carrier 1020). Such a configuration can facilitate positioning of carrier 1020 and IPG 1010 by the medical professional proximal to the one more nerves during implantation by allowing the medical professional to clearly observe and pull end 1032 while adjustment members 1024 engage retention member 1023 until carrier 1020 is secured to the desired nerve.

In particular embodiments, carrier 1020 comprises structural features to allow carrier 1020 to be secured to one or more nerves without adversely compressing the nerve. For example, as shown in FIG. 10D, the adjustment member 1024 engaged with retention member 1023 is flexible and capable of deformation when strap 1022 is secured around nerve 1002 (or multiple nerves) without adversely compressing nerve 1002. In certain embodiments, retention member 1023 may also be flexible and capable of deformation when strap 1022 is secured around nerve 1002. Furthermore, as shown in FIGS. 10D-10F in certain embodiments strap 1022 may comprise a reduced thickness portion 1026 that interfaces with nerve 1002. As shown in section view 10E, reduced thickness portion 1026 is a portion of strap 1022 that has a thickness T1 that is less than the thickness T2 of the remaining portions of strap 1022. Accordingly, reduced thickness portion 1026 can provide greater curvature of strap 1022 to allow for improved conformity to nerve 1002, thereby reducing the likelihood of excessive compression of the secured nerve. In certain embodiments T1 and/or T2 may be less than 1.0 millimeters, and may be formed from materials with a Shore A hardness of 40 or less.

The effects of an excessive nerve compression are shown in FIG. 10G, which illustrates a reduced diameter of nerve 1002 in the area engaged with strap 1022. The ability of strap 1022, retention member 1023 and/or adjustment members 1024 to sufficiently flex when engaged with nerve 1002 can allow strap 1022 to secure carrier 1020 and IPG 1010 proximal to nerve 1002 (or multiple nerves) without adversely compressing the nerve or nerves. Accordingly, such structural features can allow electrodes 1320 to sufficiently engage nerve 1002, allowing IPG 1010 to provide therapeutic benefits while reducing the potential for damage to the secured nerve or nerves.

In certain embodiments, housing 1021 can comprise additional structural features that can optimize the therapeutic benefits of IPG 1010 while reducing the risk of detrimental effects to a nerve proximal to IPG 1010. For example, as shown in the perspective view of FIG. 10A and the section view of FIG. 10F, housing 1021 comprises one or more apertures 1027 proximal to electrodes 1320. In the embodiment shown, housing 1021 also comprises one or more spacers configured to be between nerve 1002 and electrodes 1320. In particular embodiments, the spacers include a central spacer 1028 positioned between electrodes 1320. Specific embodiments can also comprise outer spacers 1029 positioned such that electrodes 1320 are positioned between outer spacers 1029. In some embodiments spacers 1028 and 1029 may be integral to housing 1021, while in other embodiments spacers 1028 and 1029 may be separate components from housing 1021.

As shown in FIG. 10F, when nerve 1002 is positioned proximal to electrodes 1320, spacers 1028 and 1029 position nerve 1002 such that nerve 1002 does not contact edges 1321 of electrodes 1320 when carrier 1020 is secured to nerve 1002. During stimulation of nerve 1002 via electrodes 1320, the current at edges 1321 of electrodes 1320 can be higher than at other portions of electrodes 1320. The increased current at edges 1321 could therefore damage nerve 1002 during activation of IPG 1010 and stimulation of nerve 1002 by electrodes 1320. Accordingly, spacers 1028 and 1029 can reduce the likelihood of damage to nerve 1002 by minimizing the potential for nerve 1002 to contacting edges 1321 of electrodes 1320.

In an example, the carrier can include a soft silicone rubber case with suturing holes that are configured to be sutured to the muscle tissue to hold the IPG in intimate contact with the hypoglossal nerve.

The carrier is configured to keep the IPG in intimate contact with the nerve. In an example, the carrier can form a cuff such as a zip tie design to allow the surgeon to adjust the size and shape to conform to the nerve. The cuff can come in different sizes to accommodate different sizes of the hypoglossal nerve or another nerve. In an example, the cuff can have a removable strap and can be made from a soft medical grade silicone rubber. In an aspect, the carrier needs to maintain contact with a 1-2 mm diameter nerve. In an aspect, the cuff is configured to attach to or be next to the underlying muscle that will contract when the nerve is stimulated. In an example, the carrier is configured to allow replacement of the IPG without replacing the carrier. The carrier should allow contraction of the muscle without creating unacceptable stresses on the nerve.

Figure 4:
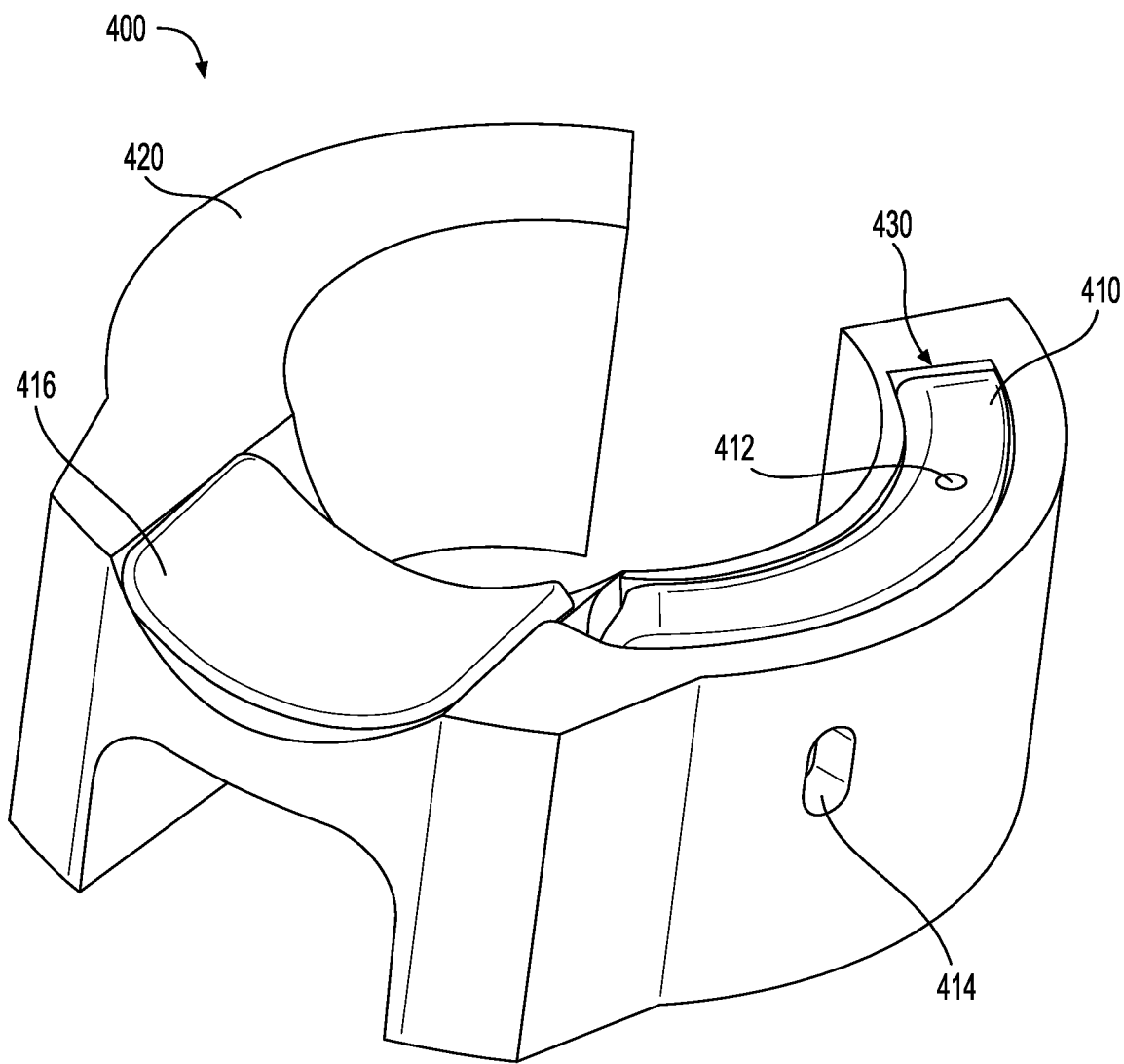
FIG. 4 is a drawing of a smart pillow or hub including a power and communication module according to an example.

Turning to FIG. 4, a smart pillow or hub 400 is shown including a power and communication module 410 according to an example. In an aspect, the hub is configured to align and hold the PCM 410 and PCM coil 416 in relation to the implanted one or more IPGs. In some implementations, the hub can be passive and only structurally or mechanically configured to align and hold the PCM in relation to the one or more implanted IPGs. In an example, the hub can include a soft cushion 420 having curvature and structure similar to a neck pillow and a holder pouch 430 configured to hold the PCM in relation to the patient and the one or more implanted IPGs. The PCM 410 can include an AUX port 412 configured to communicate with peripheral devices. The hub can include an opening 414 to access a button on the PCM.

In some implementations, hub 400 can have active components to enable or augment communication between the PCM and the IPG. In an example, the hub can have a hub coil configured to connect to the PCM and used to communicate with one or more IPGs. In an example, the hub includes a power transmitter configured to deliver power to the IPG. In an example, power transmitter can use RF energy, ultrasound energy or any other energy modality. In an example, the hub can form a band configured to be worn around the patient's neck to hold a power transmitter coil near the IPG. In an example, the hub can include a battery and is configured to power and communicate with the IPG and with the PCM. In an example, the hub can include an array of sensors configured to monitor, biosignals including but not limited to heart rate, oxygenation, movement, standing, and sound among others. The hub can include a button that communicates to the PCM.

In an example, the hub is configured to monitor efficacy and compliance. The hub can have wired or wireless connectivity to communicate information and power between the one or more smart devices and the one or more IPGs.

The hub and PCM are configured to align with the one or more IPGs in a number of ways. In an example, the PCM can send different or differential backscattering signals towards the IPGs and select the best or optimal coils and parameters based on SNR or other metrics such as least amount of power required. In an example, the hub can have multiple coils and PCM can check the optimal coil for communication.

Each battery of the hub or PCM can be charged by either a USB connector or wirelessly by induction via the coil or a battery charger. In an example, the wireless charging feature is enabled by a separate coil inside the PCM that operates at around 100-200 kHz frequencies as part of the Qi standard.

In some implementations, the hub can include a heat sink or other cooling material to prevent heating of the tissue. The cooling material can be passive or active and actively cool the hub near the patient's skin to draw heat.

In some implementations, the hub or other part of the system can include a microphone configured to listen for one or more audible cues related to breathing, snoring, environmental disturbances, and the like. In an example, the audible cue can be used to modify the treatment.

The hub can be configured for independent unilateral or bilateral control of one or more IPGs on one or more branches of the hypoglossal nerve of the patient. The hypoglossal may have multiple inclusions branches that could be independently controlled.

Figure 12:
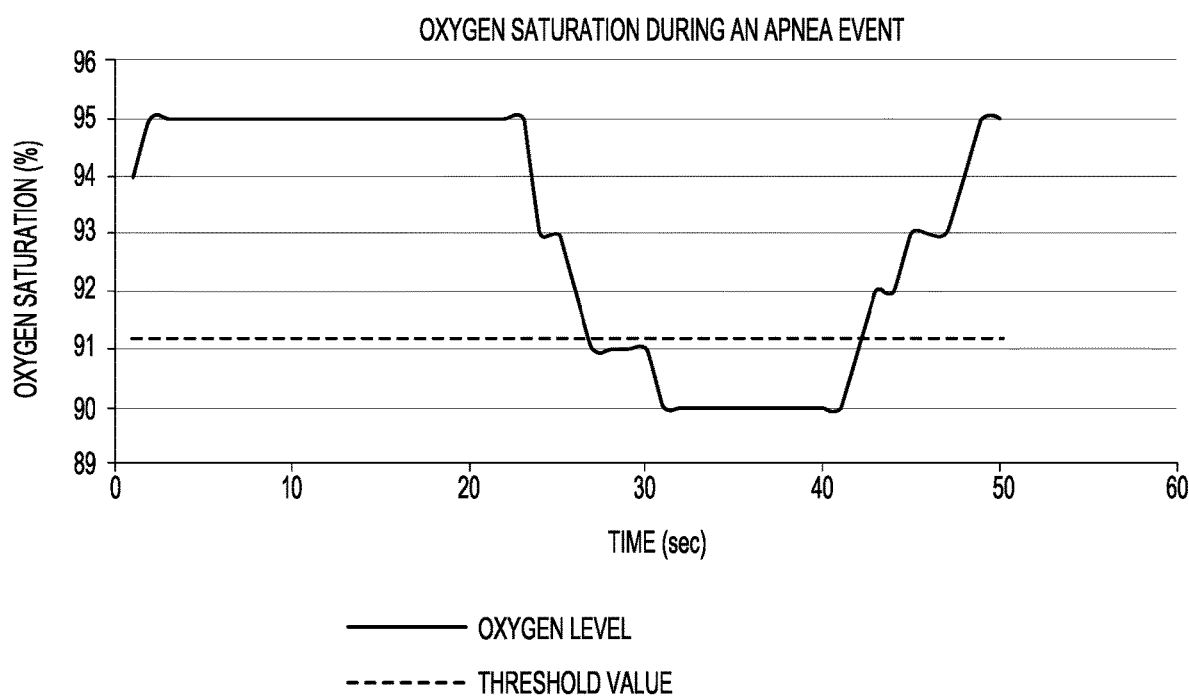
FIG. 12 is a graph of oxygen saturation during an apnea event according to an example.

Changes in oxygen saturation in obstructive sleep apnea can change on the order of seconds. In an aspect, the system is configured to receive the blood oxygenation of the patient and modify the therapy based on the oxygen saturation or SpO2 detected. In an example, the system is configured to receive blood oxygenation of the patient from another device. In some implementations, the system includes an integrated pulse oximeter 160 in either the hub or PCM to monitor the efficacy of treatment over time. The system records SpO2 and heart rate throughout the night. In an example, the hub includes a pulse oximeter configured to be in contact with the skin during sleep and measure blood oxygenation. SpO2 data will be viewable by the patient and clinician. In some implementations, the SpO2 data is used to modulate the therapy. Turning to FIG. 12, a graph of oxygen saturation is showing during an apnea event and a threshold value configured to trigger the stimulation therapy according to an example.

In an aspect, the resolution of the pulse oximeter reading may differ from those obtained from a commercial finger pulse ox during simulated sleep. For example, the resolution of the pulse oximeter may have different precision on at the neck which is closer to the carotid artery. In an example, the pulse oximetry duty cycle may differ based on the location of the sensor data.

The ReVive system is configured to run a Programming Module Application or application configured to provide the user and clinician with an interface to the IPG to program stimulation parameters, to modulate stimulation for efficacy and comfort and to review biosignals data to help assess therapy efficacy. In an example, the ReVive system includes IPG firmware configured to control the operation of the implanted IPG.

In an aspect, the application is designed with three modes: manufacturer, clinician, and user. These modes allow different levels of access to the application. In an example, the application for the patient can: check the status of the system components, set the comfort settings, set the sleep delay and turn on the system, change the ramping profile, and triggering of an exceptional event, turn on or off either of the IPGs and test stimulation, and turn on or off the acclimation mode. In an example, the application for the clinician can: perform all patient functions described above and in addition: set the acclimation settings, start current, step size, step time, set stimulation parameters, current amplitude, pulse width, frequency, set therapy parameters, set respiration rate (RR), set upper limit on RR, set lower limit on RR, and set stimulation percentage. In an example, the application for the manufacture can: perform all clinician and patient functions and in addition update firmware on the IPGs and hub.

In an embodiment, the present disclosure generally relates to methods for powering and communicating with one or more Smart Wireless Implantable Pulse Generator (SWIPG). In some embodiments, the present invention relates to programming the system to permit within night and across time acclimate of the patient to therapeutic stimulation of the hypoglossal nerve/s.

The patient may go through several sleep studies and nights in a sleep lab to manually or automatically identify a stimulation level accepted at that specific night and fine-tune the therapy, trying to reach the Therapy-Stimulation-Level. Several sleep study nights during the first months of therapy are needed to find the Therapy-Stimulation-Level. The patient may wake up easily during the sleep study nights due to the lack of acclimation to the stimulation. In this case the Therapy-Stimulation-Level is not reached, nor found, and the patients goes home with a sub-optimal level of stimulation. Another sleep study may be scheduled in order to try to find the Therapy-Stimulation-Level.

During acclimation mode, the implanted device is configured to start at a low current level and then slowly rise to a therapeutic level. The goal is for the patient to reach a level that reduces the AHI or oxygen desaturation index (ODI) within a night without causing discomfort. The Therapy-current amplitude, pulse width, frequency levels may not be accepted by the patient during the first weeks or months after the implantation of the system and first utilizations. During the acclimation period, the maximum therapy level accepted by a patient may be progressively increased night after night as the patient gets acclimated to the sensation and usage of the system and therapy.

Figure 11A:
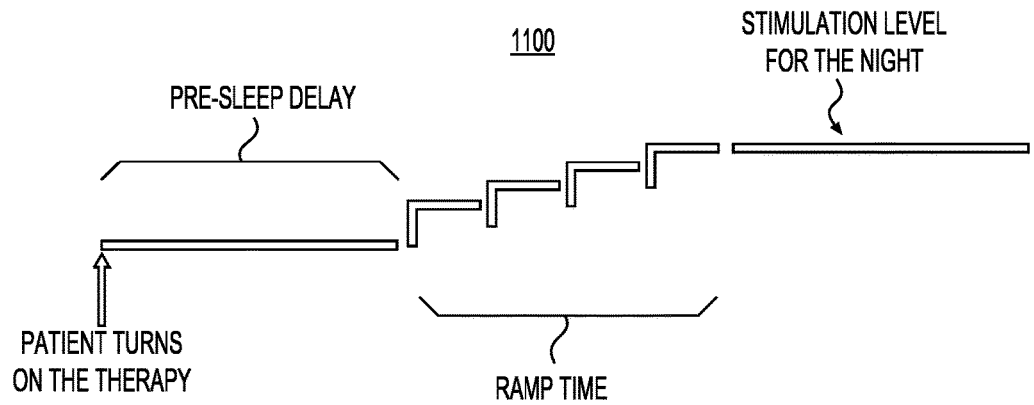
FIG. 11A is a drawing of stimulation ramp-up method when patient goes to sleep according to an example.
Figure 11B:
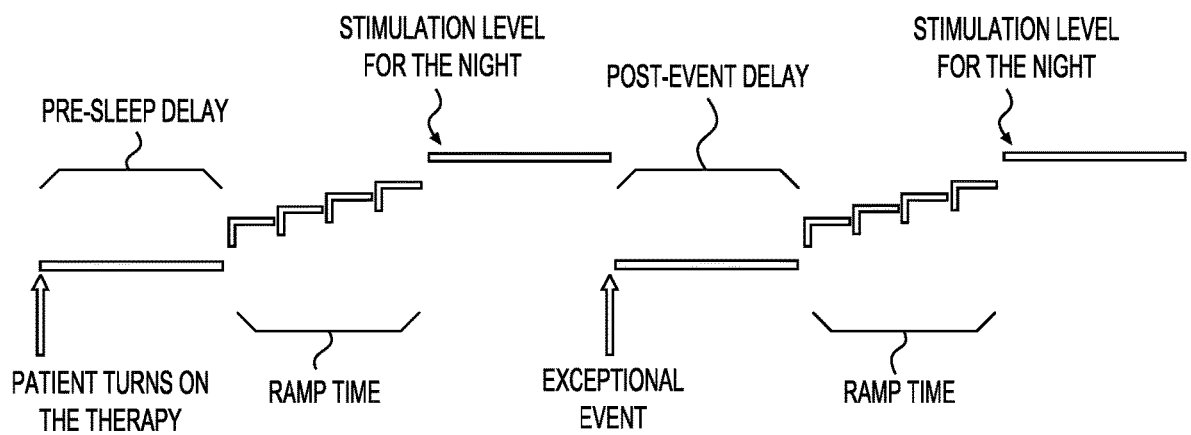
FIG. 11B is a drawing of stimulation standby method during an exceptional event according to an example.
Figure 11C:
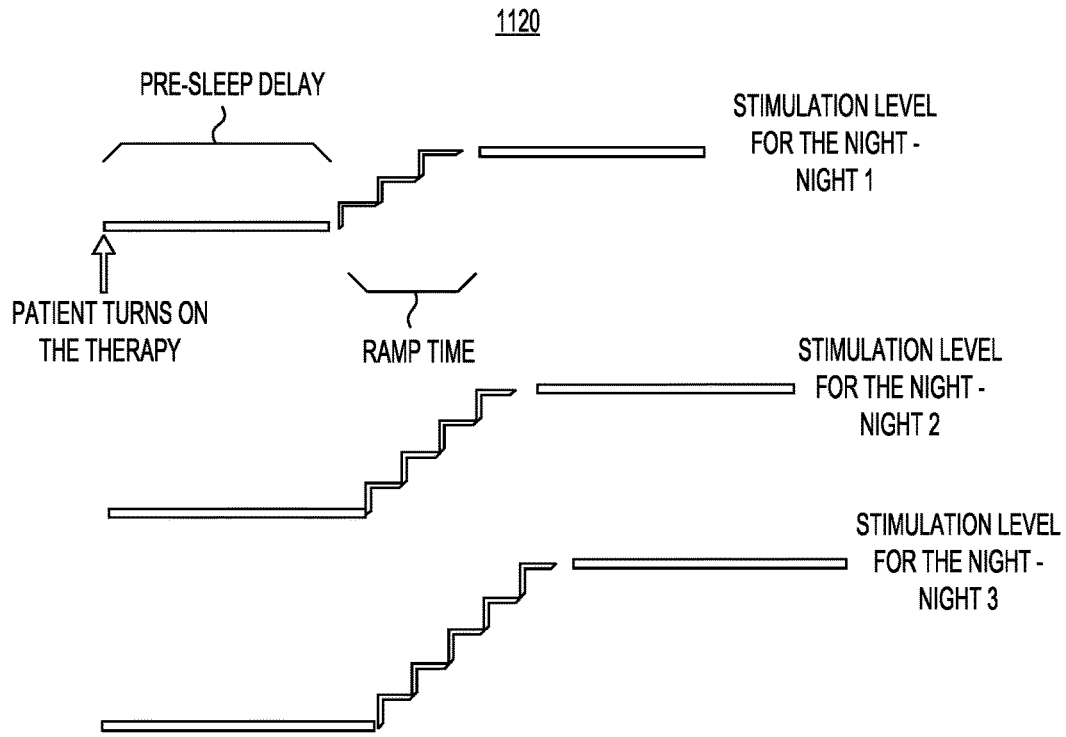
FIGS. 11C-11D are drawings of an acclimation method according to an example.
Figure 11D:
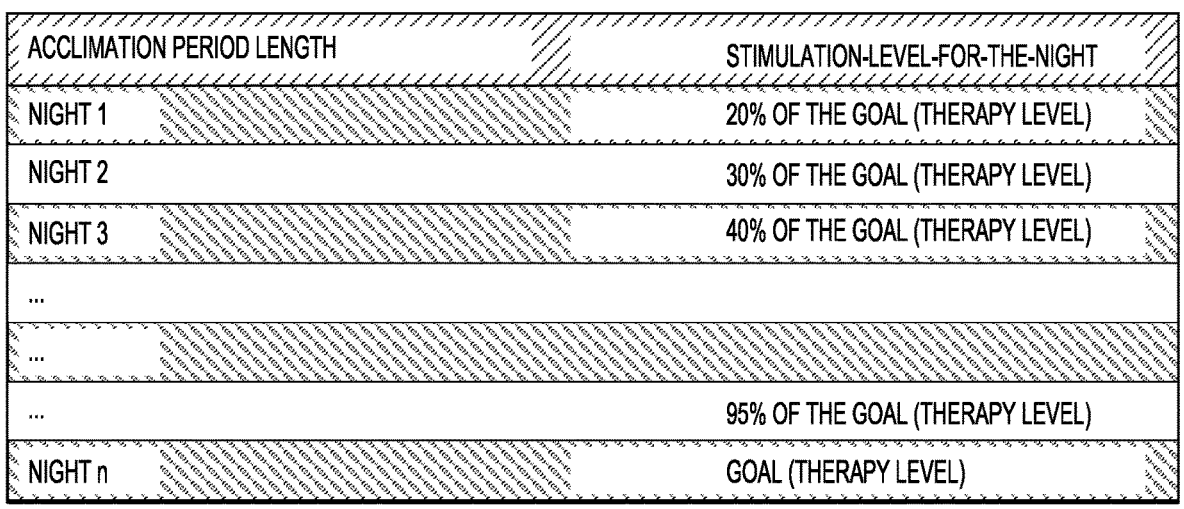

Turning to FIGS. 11C-11D, an acclimation method 1120 is shown according to an example. First, in night 1, the stimulation level is ramped up to the Stimulation-Level-For-the Night. In an example, the Stimulation-Level-For-the-Night for night 1 can be 20% of the goal or Therapy-Stimulation-Level. Next, in the next night or night 2, the stimulation level is ramped up to the Stimulation-Level-For-the-Night which includes an increment for night 2 such as an additional 10% toward the goal. Subsequent nights the stimulation level is ramped up to the Stimulation-Level-For-the-Night which includes an increment for subsequent nights.

Figure 11E:
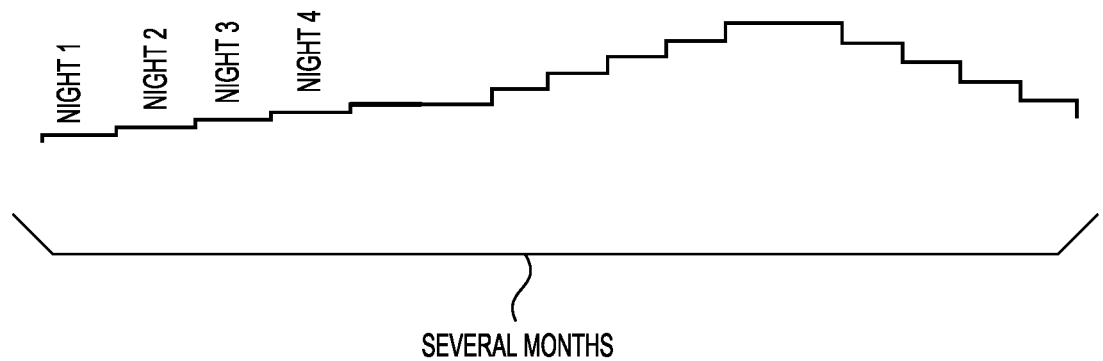
FIG. 11E is a drawing of a long-term titration method according to an example.

A long-term titration method 1140 is shown in FIG. 11E according to an example. The long-term titration method is a function of SpO2, snoring level, sleep phases, patient flow, sleep phases, as well as other biosignals. At start of the treatment, a Stimulation-Level-For-the-Night or stimulation goal for that night is calculated taking into account different bio-signals, past nights' stimulation levels, and other parameters related to the patient input, the therapy delivered in the past, etc. In an example, the calculated Stimulation-Level-For-the-Night will vary from one night to the next by a small amount of milli-Amps.

Figure 11F:
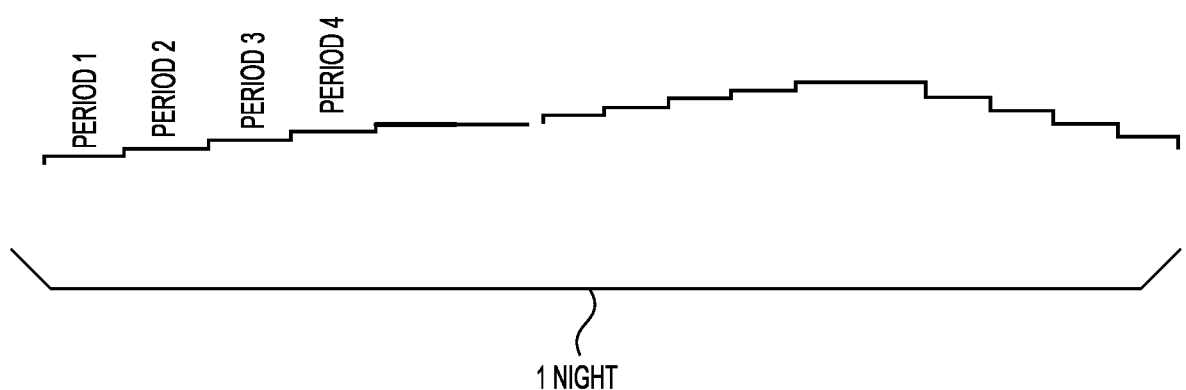
FIG. 11F is a drawing of an intra-night titration method according to an example.

An intra-night titration method 1150 is shown in FIG. 11F according to an example. At start of the treatment, a Stimulation-Level-For-the-Night or stimulation goal for that night is calculated taking into account different bio-signals, past nights' stimulation levels, and other parameters related to the patient input, the therapy delivered in the past, etc. Next, during the night, the stimulation goal for a particular moment of the night might slightly vary from the initial stimulation goal calculated in the first step with the objective of delivering the best therapy for to the patient, as well as taking into account intra-night input from the therapy. Similarly, the patient's biosignals are collected including at least one of their sleep position, sleep phase, and snoring level. In certain embodiments, the patient may be alerted if their sleep position (e.g. supine, prone or lateral) is not the correct position.

In some implementations, the PCM may be configured to implement an intra-night titration. The intra-night titration can manage an exceptional event and modify the stimulation therapy. Stimulation therapy can be modified by certain behavioral factors. In an example, the position of the patient (supine) can be used to determine that modified stimulation is needed to account for gravity of the tongue. In an example, the stimulation can be adjusted by detecting social factors such as the day of the week which can have a correlation with periodic activity. In an example, if the patient has been drinking alcohol or plans to drink alcohol, a modified AHI for a period of time can be expected and indicate a need to initiate a modified therapy.

In some implementations, the accommodation parameters are set by the clinician based on the programming session. For example, if the comfort level is 1.0 mA and efficacy level is 2.0 mA and the clinician sets the step size to 0.5 mA and the step time to 60 minutes, the system current amplitude will increase in the current in 0.5 mA steps each hour until it reaches efficacy or the user shuts the system off.

During the initial activation of any nerve the patient can experience discomfort. Over time, the stimulation current and other parameters can be increased as the patients accommodate to the higher stimulation levels. To speed up accommodation, the settings of the stimulators can be adjusted slowly during sleep.

As the patient prepares to sleep, they place the hub including the PCM around their neck and turn it on. Using an application on a programming module they can program the PCM to not start stimulation until the patient falls asleep. To avoid waking the patient from sleep, the stimulation settings start at a lower level and ramp up over time to the therapeutic dose. This slow increase in stimulation over time will permit rapid acclimation to therapeutic doses. In an example, the ramping can occur within one night or over multiple days. After about a 30 minute delay the stimulator may be configured to stimulate at 1 mA. After ~30 minutes the current may be configured to increase to 1.1 mA. Every 30 minutes the current may be configured to increase by 0.1 mA until it reached the efficacy current of 1.5 mA. The system then may be configured to stay at 1.5 mA for the remainder of the night. The next night the system may be configured to be programmed to go up to 1.6 mA or some other value if necessary. This could be repeated multiple times to maximize efficacy.

In some implementations, the starting stimulation parameters will be adjusted over time based on the oxygen desaturation index (ODI) using the SpO2 data. For example, if a review of the previous night's oxygen saturation level shows a drop of more than 3% more than 10 times per hour the current amplitude, stimulation frequency, pulse width or stimulus train duration or any combination of those parameters the next night to prevent oxygen desaturation can be modified. Examples of parameters include the size of the steps to increase the stimulation, the rate of change per unit of time of the steps to increase the stimulation, and other parameters.

In an embodiment, a system is configured for at-home use including of an external power and communication module with biosensors that monitor and record biosignals during sleep and controls one or more IPGs.

The system allows the patient and clinician to program the PCM to delay the start of stimulation and the shape of the ramp up to therapeutic doses during sleep.

In some implementations, the patient leaves home with the PCM programmed on an Acclimation Mode. The Acclimation Mode is configured to increase the level of therapy every night, in a smooth way, to get closer to an optimal therapy level, still unknown, but which it could be estimated with the thresholds found during the awake titration.

In an aspect, the optimal Therapy-Stimulation-Level-For-the-Night will vary. In an example, the patient might evolve in weight or in any other dimension that can have an influence on the number of OSA events. The PCM will collect bio signal related to the evolution of the OSA level during long time, like SpO2, snoring level, sleep phases, patient flow, sleep phases, as well as others. With this information, the PCM may compute and propose changes to the Therapy-Stimulation-Level-For-the-Night to the patient, adapted to their OSA level. The PCM will be configured to analyze oxygen saturation, movement data, electrooculogram recordings, electroencephalogram recordings and identify predictors of low oxygen levels. When oxygen desaturation occurs during a specific sleep stage, the current amplitude, stimulus duration or some combination could be increased to prevent desaturation. The patient will be able to either accept this proposition automatically, or decide yes/no every time that a new value is proposed.

During a specific night, and due to specific events, the stimulation level may vary the optimal treatment. For example, it could be that the patient needs a different stimulation level to optimally treat OSA depending on the sleep position (supine, lateral), or depending on the sleep phases, or depending on his last night eating and drinking level. By consequence, the optimal Therapy-Stimulation-Level-For-the-Night might not be a specific fixed value but could be defined as a range around an optimal value.

In some implementations, the PCM can be configured to perform a titration method taking into account patient's historic data recorded during the past nights, specific outcomes of the biosignals measured (SpO2, snoring, patient flow, sleep phase) during a specific moment of the night and compared to the recorded ones during the last nights. In an example, the patient's historic data can be used to train a Kalman filter used to determine at least one stimulation parameter. The Kalman filter can set a new level by considering information from previous nights. For example, biosignals recorded, how many times the patient adjusted the stimulation, and exceptional events. In an example, the PCM can be configured to propose changes, under specific pre-programmed limits, the Stimulation-Level-For-the-Night with the objective of optimizing the biosignals observed and by doing so better treat patient's OSA.

The Sleep Expert might have the control of this mode and may define the limits of variation of the optimal Therapy-Stimulation-Level-For-the-Night found during the Acclimation Mode, Titration Mode, and sleep study nights.

In an example, a sleep expert can implement a First Activation of the Therapy. In an example, the First Activation can include an Awake Thresholds Assessment to identify one or more thresholds related to the stimulation and acceptance by the patient. Examples of thresholds include stimulation thresholds associated with first feeling of the stimulation, first tongue movement, an effective tongue movement, and maximum discomfort for the patient. In an example, several set of parameters will be tested to define these thresholds including constant current level, pulse width, and frequency as well as others.

An example of a therapeutic setting is frequency 30 Hz, stimulation every 4 second for 2 seconds, pulse width 300 us, current will be set to 1.2 mA or at level causing tongue movement, whichever is greater. In an example, each IPG will be configured to deliver a 30 Hz, 5 mA, 300 us pulse width waveform.

In an example, the battery size should be configured to support a stimulation profile for >8 hours with stimulation a duty cycle ranging from 10% to 60% at 0.5 mA-2.5 mA, 5 Hz-30 Hz and 50 us-500 us pulse width. In an example, a larger capacity battery (>2000 mAH) can be used for higher duty cycle and longer operating times and duty cycles.

The Acclimation Mode can include a number of thresholds that can be either calculated, sensed, or imported from a patient record. Certain values can be calculated by taking into account the thresholds recorded during an Awake Thresholds Assessment. An example of the Awake Thresholds Assessment includes Day-1-Stimulation-Level-For-the-Night where a maximum or nominal stimulation level is set that the patient will receive at home for the first night or multiple nights of utilization. In another example, a Final Stimulation-Level-For-the-Night can be configured to be a stimulation level that the patient will have at home at the end of the Acclimation period. In an example, an Acclimation Period Length can be determined by a length in number of days to move from Day-1 to Final Stimulation Level. Examples of Acclimation Period Length can include a period of about 30-60 days but can be any other amount of time depending on the patient's needs.

In an example, the system can calculate an increment advancement or a number of stimulation increment steps to be added every day to the Stimulation-Level-For-the-Night. In an example, the increment advancement can take into account the level of last night, the days remaining to reach the goal, and the objective to be reached such as the Final Stimulation-Level-For-the-Night.

In some implementations, when the patient will have access to the Patient's Therapy Fine-Tuning features to modify the Stimulation-Level-For-the-Night, the Acclimation Mode will take into account the patient experience and feelings or conclusions from prior stimulation nights. The system will accept the modification of the Stimulation-Level-For-the-Night for the next night and continue to increase every night the Stimulation-Level-For-the-Night, as programed in the Acclimation Mode, in order to reach the goal set in the days/months pre-programmed.

In some implementations, a Sleep Expert can schedule an appointment with the patient based on the date that the Acclimation Mode will be reached or at the end of the First Activation of the Therapy. This will let the physician review the evolution of the Stimulation-Level-For-the-Night during the Acclimation Mode period. Also, the physician will be able to analyze the sleep related information provided by the PCM in order to assess how close the Stimulation-Level-For-the-Night reached is to the potential optimal Therapy-Stimulation-Level-For-the-Night.

With this information, the Sleep Expert might define another Acclimation Mode period or schedule a sleep study night to accurately define the Therapy-Stimulation-Level-For-the-Night, which is the stimulation level that will diminish the Apnea-Hypopnea Index to the maximum.

In an aspect, the Acclimation Mode is configured to minimize the number of sleep study nights required. In another aspect, the patient will receive every day the maximum therapy tolerated or accepted. In an example, the patient can have total control of the therapy received. At the same time managing the exceptional events will also support the patients on their progress to reach a therapy level.

In some cases, a patient can have positional apnea where the patient has apnea in certain positions. The position of the patient can be detected several ways. In an example, an accelerometer and magnetometer in the PCM or hub can be used to detect if the patient rolled over on their face. This positional information can be used to modify the therapy. In an example, the positional information can choose a stimulation profile including unilateral or bilateral or multilateral stimulation.

In an embodiment, the present disclosure generally relates to systems and methods for powering and communicating with one or more hypoglossal nerve IPGs. In some embodiments, the present disclosure relates to programming the system to permit the patient to adjust a combination of stimulation parameters on one or more smart wireless IPGs to adjust the comfort associated with stimulation.

A Comfort Control setting for at-home use includes an external power and communication module with biosensors that monitor and record biosignals during sleep and controls one or more IPGs. In an example, the Comfort Control setting allows the patient and clinician to select stimulation settings and test those settings to improve patient's comfort.

Stimulation of any nerve can be uncomfortable for the patient. However, changes in pulse width, frequency and current can alter perception of electrical stimulation of the hypoglossal nerve.

The Comfort Control setting will have a method for adjusting a combination of stimulation parameters to improve patient's comfort. The comfort settings can be independently adjusted for each IPG.

As the patients prepare to sleep, they place the PCM around their neck and turn it on. Using an application on a programming module they can press the comfort control button to change stimulation parameters. Multiple stimulation settings are pre-programed on the device. The patient can select one of the comfort settings and test that setting. The Comfort Control setting will remember that setting and use it the next time the system is activated.

In an embodiment, the stimulation level can be adjusted by the patient for fine-tuning. In an example, the patient can fine-tune the next Stimulation-Level-For-the-Night with a button either in the APP or the cuff. In an example, the patient's user interface includes a comfort button that has predefined values they can select from. In addition, they can turn off acclimation mode which will activate the comfort level for the remainder of the night. This will allow the patient to modify the therapy if it causes them to wake up during the night or cause irritation during the ramp-up of the stimulation due to a higher level of stimulation than they may tolerate at the time. In an example a number of taps on the PCM could be used to reset the acclimation mode to the initial setting without interacting with the ReVive software application. In an example, the system can record the patient adjustment and factor it in for the next stimulation program.

Sleep disordered breathing encompasses a number of illnesses including snoring, upper airway resistance syndrome (UARS) and obstructive sleep apnea-hypopnea syndrome (OSAHS). Obstructive sleep apnea (OSA) results when the tongue and soft tissue relax during sleep and move backwards in the throat resulting in partial or complete occlusion of the upper airway during sleep. If the airway occlusion persists long enough, it results in a reduction in oxygen saturation, changes in heart rate, and eventually arousing the patient from sleep. In patients with moderate to severe OSA, the airway is compromised 15 or more times per hour. Untreated, moderate to severe OSA can result in excessive daytime fatigue, poor sleep, vehicular accidents, impaired short-term memory, hypertension, right-sided congestive heart failure, stroke, and the like.

The human sleep cycle has four stages: Stage 4 is when humans exhibit rapid eye movement (REM). The other three stages are non-REM (NREM). Stage 1 is known as N1 and typically lasts 1-5 minutes. Stage 2 is known as N2 and lasts 10-60 minutes. Stage 3 is known as N3 (slow-wave sleep, delta sleep, deep sleep) and lasts 20-40 minutes. Stage 4 is REM sleep and lasts 10-60 minutes. For some patients with obstructive sleep apnea it primarily occurs during REM sleep due to the natural reduction of muscle tone in this stage. As the tongue relaxes it falls backwards and blocks the airway.

Electrical activation of any peripheral nerve can cause discomfort. A method is disclosed for monitoring the sleep stage of the patient and activating one or more of the IPGs during these stages only, configured to reduce discomfort and disrupted sleep.

During sleep the EEG, EOG, Pulse Ox, EKG, Movement sensors monitor biosignals and detect the onset of obstructive sleep apnea. For example, as snoring starts or increases in loudness the PCM activates or modifies stimulation parameters of one or more of the IPGs. A similar strategy could be used for oxygen saturation, EEG activity, heart rate changes and breathing sounds. Changes in sleep stages are used to toggle the therapy on and off.

In an embodiment, a system for at-home use includes an external power and communication module with biosensors that monitor and record one or more biosignals during sleep and controls one or more IPGs. Data from the biosensors detects changes in the sleep stage, periods of apnea-hypopnea, eye movements, or patient activity to turn on and off, or change the stimulation parameters of one or more of the IPGs. The PCM is configured to use a sleep-stage algorithm to detect sleep stage (REM), periods of apnea-hypopnea, or patient activity to activate or deactivate the system. In an example, the therapy is configured to turn on only during REM or stage 3 sleep.

Turning to FIG. 11A, a stimulation ramping profile 1100 is shown when patient goes to sleep according to an example. At an initial step the patient would wear the hub with the PCM. The PCM operating the sleep-stage algorithm will initiate a pre-sleep delay for a predetermined time. Next, the sleep-stage algorithm will activate the PCM to ramp the stimulation by sending energy to the IPG and intro the nerve target. The ramp profile can be different functions such as a step, sawtooth, linear, and exponential curve for example. In an aspect, the ramping can be based on the sleep stage, time, and condition.

In some implementations, the patient goes to bed and depending in many circumstances. It may take different amounts of time for the patient to enter different stages of sleep. In an example, the patient activates the therapy when he goes to bed: he puts on the PCM and connect all sensors needed. The system could send an initial pulse, either electrical stimulation or a haptic vibration in the hub, to the patient to indicate that everything is ready. In an example, the system will not start the stimulation until after a pre-programmed time. For example: 20 minutes, 30 min, 45 min, 1 hour. The patient will be able to change this time with the PAD application or a button on the hub. When the pre-programmed time is finalized, the system will start a ramping up to the level of stimulation parameters (a combinations of current, pulse width, etc.), by a specific % and by steps in time, for example every 5 minutes (TBC). When the system reaches the pre-programmed Stimulation-Level-For-the-Night, the stimulation remains constant during the remaining of the night. In an example, changes to the Stimulation-Level-For-the-Night could happen only if exceptional events occur. Examples of exceptional events include when the PCM detects that the patient is laying in a prone position but moving above a certain level considered normal for a sleep status, that the patient is vertical, that the patient is mobile such as walking such as for a bathroom break, or any other event programmed to change a state such as detecting a level of lucidity.

In some implementations, when an exceptional event happens, the system will pause stimulation protocols (i.e. enter stand-by). Turning to FIG. 11B, a stimulation standby-method 1110 during an exceptional event is shown according to an example. In an example, the pause will continue until there is a confirmation via one or more biosignals of the PCM that the patient is again sleeping. In an example, at that moment, the stimulation will start activating (e.g., up by steps or ramping) during a certain time, as defined above, until the system reaches a Stimulation-Level-For-the-Night. The patient may also tap one or more times or in a given pattern on the PCM to reactivate stimulation.

In some implementations, the exceptional event can be triggered manually. In an example, a patterned tapping on the hub or PCM can be detected as an input or command by the patient. For example, a double tap can be configured to reset the sleep delay. In another example, biosensors can detect movement of the patient and automatically reset the sleep delay.

At least one of the PCM and the smart device will record a log of the biosignals detected from the biosensors as well as other sensors such as the accelerometer.

In humans, the hypoglossal nerve typically bifurcates medially and laterally (Heiser, Andreas, & Benedikt, 2017). These branches innervate extrinsic muscles to control the tongue position and the intrinsic muscles control the shape of the tongue. For treatment of OSA, hypoglossal nerve stimulation is focused on activation of extrinsic muscles to move the tongue forward to open the airway. The lateral branches of the hypoglossal nerve typically innervate the extrinsic styloglossus and hyoglossus muscles. Activation of these muscles retract the tongue and can close off the airway. The medial branches of the hypoglossal nerve typically innervate the extrinsic Genioglossus oblique, genioglossus horizontal muscles. The C1 nerve typically travels within the hypoglossal nerve. This branch of C1 innervates the Geniohyoid muscle and pulls the hyoid towards the chin. This action can also open the airway.

Because human anatomy has anatomical variations the C1, medial and lateral branches may not be consistent. These nerves may also require differing stimulation parameters to activate the muscles comfortably and effectively.

It is known that some hypoglossal nerves innervate bilaterally and some only innervate the ipsilateral side. Unilateral contraction of the genioglossus muscle may reduce the efficacy of treatment. For these reasons and others, it is necessary to create an implantable system that can independently activate one or more branches of the hypoglossal and C1 nerves unilaterally or bilaterally.

In an exemplary embodiment, a method is disclosed for independently activating multiple branches of the hypoglossal and C1 nerves. This disclosure includes a fully implanted system of one or more IPGs. The IPGs can be placed on individual branches of the hypoglossal nerve and C1 nerve. The IPGs include an onboard processor that can be programmed to deliver stimulation parameters specific to the individual nerve branch. The IPGs communicate with an external power and command module that power, program, and coordinate stimulation of the individual IPGs.

In an example, a distributed system includes an external power module, a communication module, and at least one implantable pulse generator having a microprocessor configured to deliver electrical stimulation specific to a nerve branch it is connected to.

The system includes an external power and communication module and one or more IPGs. Each IPG contains a microprocessor that can be independently programmed to deliver electrical stimulation specific to the nerve branch it is connected to. The external power and communication module can selectively activate one or more IPGs to coordinate their activity to maximize efficacy.

In an example, a plurality of IPGs can be implanted, where each IPG has its own processor. The implanted devices are positioned close to or on top of 1, 2 or more branches of the XII nerve (hypoglossal nerve) and C1 nerve. In an example, the surgeon can use bipolar stimulation and recording from muscles to exclude nerve branches that retract the tongue. Each implanted device via communication with its processor, can be independently programed for at least one of current amplitude, frequency, pulse width, stimulation start time, stimulation stop time.

Each processor of the implanted device can independently communicate with an external smart device. Each processor of the implanted device can be powered with a single or multiple external coil/s in an external smart device. An external coil or multiple external coils connected to one or more external processors, can be used to power one or more processors inside the implanted devices and communicate with a single or multiple processors of the implanted devices.

In some implementations, the one or more IPGS can be configured to perform a calibration test to determine a level of cross-over, such that subsequent stimulation may be tailored to account for the cross-over. In an example, the calibration test can include identifying an anatomical variation of the nerve branches or shunt pathways from the interstitial fluid or tissue. In an example, imaging information can be used to identify calibration parameters. In an example, a laryngoscope can be used to monitor the air way opening during stimulation. Changes in stimulation parameters can be explored manually to maximize the airway opening.

In order to optimize therapy multiple IPGs may be implanted on the various nerve branches. Monitoring of biosignal data over time can be used to adjust the therapeutic doses and relative timing for each IPG.

In an exemplary embodiment, a method is disclosed for monitoring the efficacy of activation of one or more IPGs and their independently activating multiple branches of the hypoglossal and C1 nerves.

Each IPG can be placed on individual branches of the hypoglossal nerve and C1 nerve. In some implementations, each IPG have an onboard processor that can be programmed to deliver stimulation parameters specific to the individual nerve branch. In some implementations, one IPG can be configured to communicate with an external power and command module that can power, program, and coordinate stimulation of the same IPG or a different implanted IPG. In this case, the implanted IPGs may be in wired or wireless communication.

Monitoring of biosignal data can be done over one or more sleep cycles to determine the most effective method for coordinating and programing the individual IPG. The external power and communication module may include one or more biosignal sensors configured to provide an assessment of efficacy over sleep cycles. The biosignal data can include heart rate, heart rate variability, maximum heart rate, oxygen saturation, activity during sleep, sleep sounds and brain activity.

In an example, a system can be configured for at-home use consisting of an external power and communication module with biosensors that monitor and record biosignals during sleep and controls one or more IPGs. Data from the biosensors as well as the settings on the IPGs can be recorded during sleep.

In an example, a system can be configured to suggest adjustments to the coordinated activity of the IPGs based on sensed parameters including the sleep state such as REM sleep. Examples of adjustments include modifying a phase difference, the current, amplitude, frequency. In an example, the system could propose to the physician who is following the patient, to adjust specific parameters automatically, taking into account specific events recorded during the night, or the evolution of these parameters over different therapy nights, or taking into account patient's specific feedback about the quality of their sleep and quality of life. The hub is worn around the neck to position the external coil(s) to ensure consistent communication with the one or more IPGs.

In an example, the IPG is configured to run primarily open-loop while powered with the PCM. The frequency of stimulation will be set at within a range of rates and duty cycles. The goal is for the patient to entrain their breathing to when their airway is opened by hypoglossal nerve stimulation versus attempting to monitoring inspiration directly. In the case that multiple devices are implanted, they may be activated to stimulate in phase or out of phase. Each device can be programed with different stimulation parameters including at least one or more of current amplitude, pulse width, and frequency to optimize efficacy and comfort.

In some implementations, the hub and/or PCM are configured to include an array of biosensors that, independently or in coordination with the programming module application, can be used to modulate the stimulation duration the duty cycle of the stimulation. In some cases, some of these signals may lag indicators of therapy efficacy. In this case, the sensor data will be averaged over time and be used to modulate plus or minus some percentage of the current setting within safety limits. For example, if the peak heart rate over a 10-minute period is increasing, the duration of stimulation may be increased by 10%.

In an aspect, the ReVive system can have a primary safety feature that is embedded in at least one of the IPG, IPG Firmware, and the PCM. These devices will be designed to limit stimulation parameters to the predetermined safe levels. For example, the ReVive Power and Communication Module Application will be configured to not be able to set the current above the physician set level stored on the PCM or above an accepted safety level stored in the ReVive IPG firmware. In an example, the patient controls will be configured to prevent the patient from changing the stimulation levels outside of safety levels, both high and low.

In an example, the IPG can include a patient profile ID that is used to identify the patient assigned to the IPG. In an example, the patient profile ID can be programmed in the firmware or memory. The patient profile ID can prevent a hub or PCM from another patient to activate the stimulation therapy.

The system can include compliance monitoring including each time the patient wore the system. In an example, compliance monitoring can include feedback such as wearing the neck pillow correctly.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

The invention claimed is:

1. A system for providing hypoglossal stimulation, the system comprising:
    a first pulse generator, wherein the first pulse generator comprises: at least a first electrode and a second electrode;
    a pulse generator coil; and
    circuitry configured to receive an energy signal, the first pulse generator configured to be implanted directly on a hypoglossal nerve on a first side of the patient and configured to deliver stimulation energy to activate at least one branch of the hypoglossal nerve on the first side of the patient;
    a communication module including a communication coil configured to communicate with the pulse generator coil;
    a programming module configured to communicate programming instructions to the communication module, the programming instructions defining an attribute of the stimulation energy, wherein:
    at least one of the communication module and the programming module is configured to receive sensor data from a first sensor configured to sense at least one of heart rate, oxygen saturation, sleep sounds, patient movement, eye movement, and electrical activity of at least one of the brain and eye, and
    the attribute of the stimulation energy includes at least one of a current amplitude, current duration, a ramping profile, and a pause; and
    a carrier configured to couple to the pulse generator and to secure the pulse generator to the hypoglossal nerve, the carrier comprising at least one spacer proximal to an aperture, a strap comprising a plurality of adjustment members, and a retention member configured to engage the plurality of adjustment members.

2. The system of claim 1, wherein the pulse generator does not comprise a battery.

3. The system of claim 1, wherein the attribute of the stimulation energy further includes at least one of a pulse width, pulse frequency, specified waveform shapes, rise time and fall time.

4. The system of claim 1, wherein the programming module is configured to adjust the attribute of the stimulation energy during a single night.

5. The system of claim 1, wherein the programming module is configured to adjust the attribute of the stimulation energy during multiple nights.

6. The system of claim 1, wherein the sensor data further comprises a sleep position of the patient and wherein the system is configured to alert the patient when the sleep position is not the correct sleep position.

7. The system of claim 1, wherein the system is configured to calculate an oxygen desaturation index (ODI) or a Apnea-Hypopnea Index (AHI), and wherein the attribute of the stimulation energy is adjusted based on the ODI or the AHI.

8. The system of claim 1, wherein:
the first electrode and the second electrode each comprise a plurality of edges; and
the at least one spacer is configured to position a hypoglossal nerve such that the hypoglossal nerve does not contact the plurality of edges of the first electrode and the second electrode when the carrier is secured to the hypoglossal nerve.

9. The system of claim 1, wherein the at least one spacer comprises a central spacer between the first electrode and the second electrode.

10. The system of claim 1, wherein the pulse generator comprises a microprocessor.

11. The system of claim 1, the system further comprising a second pulse generator, having no battery, including at least a first and second electrode, a second pulse generator coil, and circuitry configured to receive an energy signal, the second pulse generator configured to be implanted directly on a hypoglossal nerve on a second side of the patient and configured to deliver stimulation energy to activate at least one branch of the hypoglossal nerve on the second side of the patient.

12. The system of claim 11, the system further comprising a second sensor configured to detect a position of the patient;
wherein the programming module is configured to modify the stimulation energy on at least one of the first pulse generator and the second pulse generator based on the position of the patient.

13. The system of claim 1, the system further comprising a second pulse generator, having no battery, including at least a first and second electrode, a second pulse generator coil, and circuitry configured to receive an energy signal;
wherein the second pulse generator is configured to be implanted directly on the hypoglossal nerve on a second branch of the hypoglossal nerve on the first side of the patient and configured to deliver stimulation energy to activate at least another branch of the hypoglossal nerve on the first side of the patient.

14. The system of claim 1, wherein the pulse generator comprises an aperture configured to receive a strap to secure the pulse generator to the hypoglossal nerve.

15. The system of claim 1, wherein the energy signal is at least one of electromagnetic energy and ultrasound energy.

16. The system of claim 1, wherein the pulse generator coil is a mechanical structure configured to transform ultrasound energy to generate the stimulation energy to activate the at least one branch of the hypoglossal nerve.

17. The system of claim 1, further comprising a wearable hub configured to position the communication module in relation to the pulse generator such that the pulse generator coil substantially aligns with the communication coil.

18. The system of claim 17, wherein the wearable hub comprises a hub coil configured align with the pulse generator coil and a second hub coil the communication module to position the communication module in relation to the pulse generator such that the pulse generator coil substantially aligns with the communication coil.

19. The system of claim 17, wherein the wearable hub comprises a hub coil configured align with the pulse generator coil and at least one of a second hub coil configured to align with the communication module and a wired connection.

20. The system of claim 17, further comprising a hub configured to hold the first sensor to the skin of the patient, such that the first sensor can obtain a physiological reading.

21. A system for providing hypoglossal stimulation, the system comprising:
a first pulse generator, wherein the first pulse generator comprises: at least a first electrode and a second electrode;
a pulse generator coil;
circuitry configured to receive an energy signal, the first pulse generator configured to be implanted directly on a hypoglossal nerve on a first side of the patient and configured to deliver stimulation energy to activate at least one branch of the hypoglossal nerve on the first side of the patient;
a communication module including a communication coil configured to communicate with the pulse generator coil;
a programming module configured to communicate programming instructions to the communication module, the programming instructions defining an attribute of the stimulation energy, wherein:
at least one of the communication module and the programming module is configured to receive sensor data from a first sensor configured to sense at least one of heart rate, oxygen saturation, sleep sounds, patient movement, eye movement, and electrical activity of at least one of the brain and eye, and the attribute of the stimulation energy includes at least one of a current amplitude, current duration, a ramping profile, and a pause; and
a carrier configured to couple to the pulse generator and to secure the pulse generator to the hypoglossal nerve, the carrier including a body portion configured to secure the pulse generator to at least a first branch of the hypoglossal nerve and an arm portion extending from the body portion configured to isolate at least a second branch of the hypoglossal nerve from the first branch of the hypoglossal nerve.

22. The system of claim 21, wherein the pulse generator does not comprise a battery.

23. The system of claim 21, wherein the attribute of the stimulation energy includes at least one of a pulse width, pulse frequency, specified waveform shapes, rise time and fall time.

24. The system of claim 21, wherein the programming module is configured to adjust the attribute of the stimulation energy during a single night.

25. The system of claim 21, wherein the sensor data comprises a sleep position of the patient and wherein the system is configured to alert the patient when the sleep position is not the correct sleep position.

26. The system of claim 21, wherein the carrier further includes a housing having at least one spacer, a strap comprising a plurality of adjustment members, and a retention member configured to engage the plurality of adjustment members.

27. The system of claim 26, wherein:
the first electrode and the second electrode each comprise a plurality of edges; and
the at least one spacer is configured to position a hypoglossal nerve such that the hypoglossal nerve does not contact the plurality of edges of the first electrode and the second electrode when the carrier is secured to the hypoglossal nerve.

28. The system of claim 26, wherein the at least one spacer comprises a central spacer between the first electrode and the second electrode.

29. The system of claim 21, the system further comprising a second pulse generator, having no battery, including at least a first and second electrode, a second pulse generator coil, and circuitry configured to receive an energy signal; and
   wherein the second pulse generator is configured to be implanted directly on the hypoglossal nerve on a second branch of the hypoglossal nerve on the first side of the patient and configured to deliver stimulation energy to activate at least another branch of the hypoglossal nerve on the first side of the patient.

30. The system of claim 21, wherein the pulse generator comprises an aperture configured to receive a strap to secure the pulse generator to the hypoglossal nerve.

31. The system of claim 21, wherein the energy signal is at least one of electromagnetic energy and ultrasound energy.

32. The system of claim 21, wherein the pulse generator coil is a mechanical structure configured to transform ultrasound energy to generate the stimulation energy to activate the at least one branch of the hypoglossal nerve.

33. The system of claim 21, further comprising a wearable hub configured to position the communication module in relation to the pulse generator such that the pulse generator coil substantially aligns with the communication coil.

34. The system of claim 33, wherein the wearable hub is configured to hold the first sensor to the skin of the patient, such that the first sensor can obtain a physiological reading.

* * * * *